(12) United States Patent
Hong

(10) Patent No.: US 10,531,655 B2
(45) Date of Patent: Jan. 14, 2020

(54) REPERFUSION PROTECTION SOLUTION AND USES THEREOF

(71) Applicant: The Regents of the University of California, Oakland, CA (US)

(72) Inventor: Johnny C. Hong, Fox Point, WI (US)

(73) Assignee: The Regents of the University of California, Oakland, CA (US)

(*) Notice: Subject to any disclaimer, the term of this patent is extended or adjusted under 35 U.S.C. 154(b) by 628 days.

(21) Appl. No.: 14/360,863

(22) PCT Filed: Nov. 30, 2012

(86) PCT No.: PCT/US2012/067348
§ 371 (c)(1),
(2) Date: May 27, 2014

(87) PCT Pub. No.: WO2013/082458
PCT Pub. Date: Jun. 6, 2013

(65) Prior Publication Data
US 2014/0329221 A1  Nov. 6, 2014

Related U.S. Application Data

(60) Provisional application No. 61/566,419, filed on Dec. 2, 2011.

(51) Int. Cl.
*A01N 1/02* (2006.01)
(52) U.S. Cl.
CPC .................. *A01N 1/0226* (2013.01)
(58) Field of Classification Search
None
See application file for complete search history.

(56) References Cited

U.S. PATENT DOCUMENTS

| | | | |
|---|---|---|---|
| 4,988,515 A * | 1/1991 | Buckberg | A61K 33/06 424/529 |
| 5,002,965 A | 3/1991 | Ramwell et al. | |
| 5,025,032 A | 6/1991 | Carney et al. | |
| 5,057,494 A | 10/1991 | Sheffield | |
| 5,212,071 A | 5/1993 | Fearon et al. | |
| RE35,112 E | 12/1995 | Carney et al. | |
| 5,472,939 A | 12/1995 | Fearon et al. | |
| 5,498,427 A * | 3/1996 | Menasche | A01N 1/02 424/678 |
| 5,520,912 A | 5/1996 | Eibl et al. | |
| 5,552,267 A * | 9/1996 | Stern | A01N 1/0226 435/1.1 |
| 5,661,188 A | 8/1997 | Weissman et al. | |
| 5,674,708 A | 10/1997 | Cooperman et al. | |
| 5,693,462 A * | 12/1997 | Raymond | A01N 1/0226 435/1.2 |
| 5,981,481 A | 11/1999 | Fearon et al. | |
| 6,214,035 B1 | 4/2001 | Streeter | |
| 6,277,990 B1 | 8/2001 | Jagtap et al. | |
| 6,316,604 B1 | 11/2001 | Fearon et al. | |
| 6,437,165 B1 | 8/2002 | Mandala et al. | |
| 6,534,651 B2 | 3/2003 | Jagtap et al. | |
| 6,599,283 B1 | 7/2003 | Marzilli et al. | |
| 6,924,267 B2 | 8/2005 | Daemen et al. | |
| 6,967,254 B2 | 11/2005 | Dominguez et al. | |
| 7,026,326 B2 | 4/2006 | Cao et al. | |
| 7,049,318 B2 | 5/2006 | Dominguez et al. | |
| 7,419,663 B2 | 9/2008 | Ashkenazi et al. | |
| 7,429,594 B2 | 9/2008 | Liu et al. | |
| 7,504,403 B2 | 3/2009 | Frohn et al. | |
| 7,635,386 B1 | 12/2009 | Gammie | |
| 7,837,650 B1 | 11/2010 | Cox et al. | |
| 7,956,037 B2 | 6/2011 | Peterson | |
| 7,985,536 B2 | 7/2011 | Brasile | |
| 8,262,612 B1 | 9/2012 | Cox et al. | |
| 2001/0041170 A1 | 11/2001 | Winchell et al. | |
| 2001/0048924 A1 | 12/2001 | Del Zoppo | |
| 2001/0053790 A1 | 12/2001 | Mangat et al. | |
| 2002/0029037 A1 | 3/2002 | Kim et al. | |
| 2002/0055468 A1 | 5/2002 | Oeltgen et al. | |
| 2002/0095044 A1 | 7/2002 | Jagtap et al. | |
| 2002/0122796 A1 | 9/2002 | Cummings et al. | |
| 2002/0128211 A1 | 9/2002 | Yoshikawa et al. | |

(Continued)

FOREIGN PATENT DOCUMENTS

| AU | 8906791 A1 | 6/1992 |
|---|---|---|
| AU | 1748092 A1 | 11/1992 |

(Continued)

OTHER PUBLICATIONS

Petrat (Glycine, a simple physiological compound protecting by yet puzzling mechanisms against ischemia reperfusion injury, 2011).*
Butter (Effect of Glycine on Isolated, Perfused Rabbit Livers Following 48-hour preservation in UW solution without Glutathione, 1994).*
Cuesta (Fructose 1,6-bisphosphate prevented endotoxemia, macrophage activation, and liver injury induced by D-galactosamine in rats, 2006).*
PCT International Search Report and Written Opinion dated Mar. 18, 2013 issued in PCT/US2012/067348.
PCT International Preliminary Report on Patentability dated Jun. 3, 2014 issued in PCT/US2012/067348.
Allen, et al. (2004) "Pediatric myocardial protection: a cardioplegic strategy is the 'solution'" *Pediatric Cardiac Surgery Arumal of the Seminnars in Thoracic Cardiovascular Surgery*, 7: 141-154.
Beyersdorf et al. (1989) "Studies on prolonged acute regional ischemia: I. Evidence for preserved cellular viability after 6 hours of coronary occlusion" *J. Thorac. Cardiovasc. Surg.*, 98: 112-126 [Abstract Only].

(Continued)

*Primary Examiner* — Nghi V Nguyen
(74) *Attorney, Agent, or Firm* — Tom Hunter; Weaver Austin Villeneuve & Sampson LLP

(57) ABSTRACT

In various embodiments a reperfusion protection solution (RPS) is provided along with methods of use thereof. Illustrative reperfusion protection solutions include, but are not limited to a buffer; one or more substrates for the synthesis of adenosine triphosphate (ATP) under anaerobic conditions; citrate-phosphate-dextrose (CPD); and one or more amino acids that stabilize cell membranes. Typically the pH of the organ reperfusion protection solution ranges from about pH 8.1 to about pH 8.4.

13 Claims, 8 Drawing Sheets

(56) References Cited

U.S. PATENT DOCUMENTS

| | | |
|---|---|---|
| 2002/0187492 A1 | 12/2002 | Todderud et al. |
| 2003/0040502 A1 | 2/2003 | Salzman et al. |
| 2003/0040531 A1 | 2/2003 | Fujishima et al. |
| 2003/0053998 A1 | 3/2003 | Daemen et al. |
| 2003/0069174 A1 | 4/2003 | Pichler et al. |
| 2003/0073743 A1 | 4/2003 | Ajami et al. |
| 2003/0096833 A1 | 5/2003 | Jagtap et al. |
| 2003/0109433 A1 | 6/2003 | Oeltgen et al. |
| 2003/0113744 A1 | 6/2003 | O'Toole et al. |
| 2003/0118578 A1 | 6/2003 | Rosenzweig et al. |
| 2003/0138420 A1 | 7/2003 | Del Zoppo |
| 2003/0149050 A1 | 8/2003 | Jagtap et al. |
| 2003/0166243 A1 | 9/2003 | Cope et al. |
| 2003/0181353 A1 | 9/2003 | Nyce |
| 2003/0211998 A1 | 11/2003 | Oeltgen et al. |
| 2003/0216424 A1 | 11/2003 | Davis |
| 2003/0216582 A1 | 11/2003 | Nikolaides et al. |
| 2004/0038192 A1 | 2/2004 | Brasile |
| 2004/0038891 A1 | 2/2004 | Bisgaier et al. |
| 2004/0047861 A1 | 3/2004 | Kehrel et al. |
| 2004/0092447 A1 | 5/2004 | Cornell-Bell et al. |
| 2004/0131607 A1 | 7/2004 | Carroll et al. |
| 2004/0132666 A1 | 7/2004 | Neuwelt et al. |
| 2004/0158067 A1 | 8/2004 | Hutchison et al. |
| 2004/0192596 A1 | 9/2004 | Petzelbauer |
| 2004/0254178 A1 | 12/2004 | Dominguez et al. |
| 2004/0255956 A1 | 12/2004 | Vinten-Johansen et al. |
| 2005/0009918 A1 | 1/2005 | Wen et al. |
| 2005/0014715 A1 | 1/2005 | Salzman et al. |
| 2005/0019744 A1 | 1/2005 | Bertuglia |
| 2005/0020592 A1 | 1/2005 | Dominguez et al. |
| 2005/0037995 A1 | 2/2005 | Lockwood et al. |
| 2005/0038010 A1 | 2/2005 | Cao et al. |
| 2005/0043301 A1 | 2/2005 | Liu et al. |
| 2005/0059738 A1 | 3/2005 | Ajami et al. |
| 2005/0065097 A1 | 3/2005 | Lockwood et al. |
| 2005/0089507 A1 | 4/2005 | Mehta et al. |
| 2005/0143475 A1 | 6/2005 | Lockwood et al. |
| 2005/0187221 A1 | 8/2005 | Matsuda et al. |
| 2005/0187223 A1 | 8/2005 | Frohn et al. |
| 2005/0203065 A1 | 9/2005 | Smits et al. |
| 2005/0214295 A1 | 9/2005 | Paul et al. |
| 2005/0214308 A1 | 9/2005 | Ashkenazi et al. |
| 2005/0215533 A1 | 9/2005 | Gottlieb et al. |
| 2005/0222038 A1 | 10/2005 | Oeltgen et al. |
| 2005/0266391 A1 | 12/2005 | Bennett et al. |
| 2005/0267143 A1 | 12/2005 | Davis et al. |
| 2005/0288502 A1 | 12/2005 | Andersen et al. |
| 2006/0002944 A1 | 1/2006 | Ashkenazi et al. |
| 2006/0029589 A1 | 2/2006 | Weiler |
| 2006/0034801 A1 | 2/2006 | Jalkanen |
| 2006/0040312 A1 | 2/2006 | Cornell-bell et al. |
| 2006/0051407 A1 | 3/2006 | Richter et al. |
| 2006/0067925 A1 | 3/2006 | Labhasetwar et al. |
| 2006/0069110 A1 | 3/2006 | Andersen et al. |
| 2006/0100639 A1 | 5/2006 | Levin et al. |
| 2006/0111421 A1 | 5/2006 | Chadwick et al. |
| 2006/0140939 A1 | 6/2006 | Fung |
| 2006/0148700 A1 | 7/2006 | Mochly-rosen et al. |
| 2006/0161001 A1 | 7/2006 | Hong et al. |
| 2006/0167021 A1 | 7/2006 | Losordo |
| 2006/0205671 A1 | 9/2006 | Vinten-johansen |
| 2006/0234986 A1 | 10/2006 | Buckman et al. |
| 2006/0247263 A1 | 11/2006 | Siegmund |
| 2006/0263351 A1 | 11/2006 | Lo et al. |
| 2007/0054855 A1 | 3/2007 | Allison |
| 2007/0072862 A1 | 3/2007 | Dimauro et al. |
| 2007/0142294 A1 | 6/2007 | Todderud et al. |
| 2007/0148628 A1* | 6/2007 | Young .................. A01N 1/0226 435/1.1 |
| 2007/0160645 A1 | 7/2007 | Vinten-johansen |
| 2007/0169779 A1 | 7/2007 | Freeman |
| 2007/0190054 A1 | 8/2007 | Ashkenazi et al. |
| 2007/0207150 A1 | 9/2007 | Allison |
| 2007/0212701 A1 | 9/2007 | O'toole et al. |
| 2007/0258945 A1 | 11/2007 | Mehta et al. |
| 2007/0259032 A1 | 11/2007 | Bright et al. |
| 2007/0280930 A1 | 12/2007 | Rouschop et al. |
| 2007/0293436 A1 | 12/2007 | Peterson et al. |
| 2008/0004207 A1 | 1/2008 | Tsung et al. |
| 2008/0017202 A1 | 1/2008 | Michal et al. |
| 2008/0069823 A1 | 3/2008 | Allison |
| 2008/0069883 A1 | 3/2008 | Wen et al. |
| 2008/0091140 A1 | 4/2008 | Hamburger |
| 2008/0096184 A1 | 4/2008 | Brasile |
| 2008/0104718 A1 | 5/2008 | Berk et al. |
| 2008/0139497 A1 | 6/2008 | Yang |
| 2008/0153910 A1 | 6/2008 | Datta et al. |
| 2008/0161303 A1 | 7/2008 | Zhang et al. |
| 2008/0200645 A1 | 8/2008 | Kotwal et al. |
| 2008/0227733 A1 | 9/2008 | Lieberman et al. |
| 2008/0248118 A1 | 10/2008 | Labhasetwar et al. |
| 2008/0254037 A1 | 10/2008 | Linden et al. |
| 2008/0255217 A1 | 10/2008 | Yabe et al. |
| 2008/0305993 A1 | 12/2008 | Mannesse et al. |
| 2009/0011987 A1 | 1/2009 | Olsen |
| 2009/0012299 A1 | 1/2009 | Pettus et al. |
| 2009/0017031 A1 | 1/2009 | Fung |
| 2009/0036400 A1 | 2/2009 | Haehner et al. |
| 2009/0042807 A1 | 2/2009 | Khan et al. |
| 2009/0076105 A1 | 3/2009 | Chung et al. |
| 2009/0081211 A1 | 3/2009 | Campagne |
| 2009/0104182 A1 | 4/2009 | Kluxen et al. |
| 2009/0137582 A1 | 5/2009 | Pettus et al. |
| 2009/0191262 A1 | 7/2009 | Mueller-enoch et al. |
| 2009/0221649 A1 | 9/2009 | Krahn et al. |
| 2009/0298822 A1 | 12/2009 | Krahn et al. |
| 2010/0028417 A1 | 2/2010 | Mueller-enoch et al. |
| 2010/0160367 A1 | 6/2010 | Davis et al. |
| 2010/0160444 A1 | 6/2010 | Gottlieb et al. |
| 2010/0197758 A1 | 8/2010 | Andrews et al. |
| 2010/0209532 A1 | 8/2010 | Dube et al. |
| 2010/0233168 A1 | 9/2010 | Wanderer |
| 2010/0266567 A1 | 10/2010 | Linz et al. |
| 2010/0292234 A1 | 11/2010 | Pettus et al. |
| 2010/0292313 A1 | 11/2010 | Baguisi et al. |
| 2010/0305183 A1 | 12/2010 | Nimmo et al. |
| 2010/0331760 A1 | 12/2010 | Atanasoska et al. |
| 2010/0331775 A1 | 12/2010 | Atanasoska et al. |
| 2011/0014270 A1 | 1/2011 | Holers et al. |
| 2011/0040221 A1 | 2/2011 | Mcnulty et al. |
| 2011/0046207 A1 | 2/2011 | Purschke et al. |
| 2011/0105498 A1 | 5/2011 | Pettus et al. |
| 2011/0105499 A1 | 5/2011 | Tasker |
| 2011/0118197 A1 | 5/2011 | Chaturvedi |
| 2011/0120471 A1 | 5/2011 | Freeman |
| 2011/0130334 A1 | 6/2011 | Huang et al. |
| 2011/0135665 A1 | 6/2011 | Gudkov et al. |
| 2011/0160294 A1 | 6/2011 | Baguisi et al. |
| 2011/0190206 A1 | 8/2011 | Huang et al. |
| 2011/0218144 A1 | 9/2011 | Baker et al. |
| 2011/0229433 A1 | 9/2011 | Kungl et al. |
| 2011/0230765 A1 | 9/2011 | Guracar |
| 2011/0238107 A1 | 9/2011 | Raheman |
| 2011/0262456 A1 | 10/2011 | Bansal |
| 2011/0270174 A1 | 11/2011 | Ehrenreich et al. |
| 2011/0270175 A1 | 11/2011 | Ehrenreich et al. |
| 2011/0270176 A1 | 11/2011 | Ehrenreich et al. |
| 2011/0275629 A1 | 11/2011 | Pettus et al. |
| 2011/0281837 A1 | 11/2011 | Hutchinson et al. |
| 2011/0281864 A1 | 11/2011 | Pettus et al. |
| 2011/0293601 A1 | 12/2011 | Heffernan et al. |
| 2011/0294805 A1 | 12/2011 | Pettus et al. |
| 2011/0301571 A1 | 12/2011 | Guimaraes |
| 2011/0306556 A1 | 12/2011 | Dawson-scully et al. |
| 2011/0312902 A1 | 12/2011 | Peterson |
| 2011/0319330 A1 | 12/2011 | Shapiro |
| 2011/0319866 A1 | 12/2011 | Consigny et al. |
| 2012/0040983 A1 | 2/2012 | Tasker et al. |
| 2012/0064044 A1 | 3/2012 | Egan |
| 2012/0088728 A1 | 4/2012 | Mannesse et al. |
| 2012/0108587 A1 | 5/2012 | Tasker et al. |
| 2012/0122870 A1 | 5/2012 | Smith et al. |
| 2012/0122873 A1 | 5/2012 | Mesangeau et al. |

(56) References Cited

U.S. PATENT DOCUMENTS

| | | |
|---|---|---|
| 2012/0123509 A1 | 5/2012 | Merrill et al. |
| 2012/0128674 A1 | 5/2012 | Campagne |
| 2012/0129188 A1 | 5/2012 | Gazmuri |
| 2012/0135932 A1 | 5/2012 | Baguisi et al. |
| 2012/0141466 A9 | 6/2012 | Heffernan et al. |
| 2012/0148560 A1 | 6/2012 | Dawson-scully et al. |
| 2012/0189626 A1 | 7/2012 | Ashkenazi et al. |
| 2012/0213798 A1 | 8/2012 | Levy et al. |
| 2012/0219596 A1 | 8/2012 | Limbach et al. |
| 2012/0265283 A1 | 10/2012 | Mack et al. |
| 2012/0330199 A1 | 12/2012 | Lurie et al. |
| 2013/0004515 A1 | 1/2013 | Gudkov et al. |
| 2013/0005658 A1 | 1/2013 | Olson et al. |
| 2013/0078235 A1 | 3/2013 | Zhou |
| 2013/0108715 A1 | 5/2013 | Kobayashi et al. |
| 2013/0143828 A1 | 6/2013 | Molteni |
| 2013/0171236 A1 | 7/2013 | Holers et al. |
| 2013/0218196 A1 | 8/2013 | Cheung |
| 2013/0244941 A1 | 9/2013 | Mannesse et al. |
| 2013/0281897 A1 | 10/2013 | Hoffmann et al. |
| 2014/0024715 A1 | 1/2014 | Peterson |
| 2014/0025143 A1 | 1/2014 | Atkinson et al. |
| 2014/0100278 A1 | 4/2014 | Limbach et al. |
| 2014/0178465 A1 | 6/2014 | Bright et al. |
| 2014/0220037 A1 | 8/2014 | Gudkov et al. |
| 2014/0228407 A1 | 8/2014 | Appelbaum et al. |
| 2014/0274917 A1 | 9/2014 | Baguisi et al. |
| 2014/0336118 A1 | 11/2014 | Treiman et al. |
| 2014/0336120 A1 | 11/2014 | Mangat et al. |
| 2014/0336183 A1 | 11/2014 | Mangat et al. |
| 2014/0363391 A1 | 12/2014 | Yannopoulos et al. |
| 2015/0005227 A1 | 1/2015 | Cohen et al. |
| 2015/0080388 A1 | 3/2015 | Guarna et al. |
| 2015/0126973 A1 | 5/2015 | Cox et al. |
| 2015/0157816 A1 | 6/2015 | Freeman et al. |
| 2015/0174123 A1 | 6/2015 | Kovach et al. |
| 2015/0182587 A1 | 7/2015 | Gudkov et al. |
| 2015/0202219 A1 | 7/2015 | Dawson-scully et al. |
| 2015/0209304 A1 | 7/2015 | Huang et al. |
| 2015/0309013 A1 | 10/2015 | Park et al. |
| 2015/0374667 A1 | 12/2015 | Mangat et al. |
| 2016/0008442 A1 | 1/2016 | Spirig et al. |
| 2016/0015771 A1 | 1/2016 | Sieg |
| 2016/0050909 A1 | 2/2016 | Deckelbaum et al. |
| 2016/0058305 A1 | 3/2016 | Graham et al. |

FOREIGN PATENT DOCUMENTS

| | | |
|---|---|---|
| AU | 3222893 A1 | 6/1993 |
| AU | 661980 B2 | 8/1995 |
| CA | 2095606 A1 | 5/1992 |
| CA | 1340866 A1 | 12/1999 |
| CA | 2067744 C | 2/2001 |
| CA | 1341443 A1 | 10/2003 |
| CA | 2564263 A1 | 4/2008 |
| CN | 1954825 B | 5/2007 |
| EP | 0357240 B1 | 12/1993 |
| EP | 0559677 B1 | 9/1996 |
| EP | 0913470 A3 | 9/1999 |
| EP | 1229034 A1 | 8/2002 |
| EP | 1250935 A1 | 10/2002 |
| EP | 0411031 B1 | 5/2003 |
| EP | 0973392 B1 | 11/2003 |
| EP | 1448564 B1 | 4/2006 |
| EP | 1542680 B1 | 3/2007 |
| EP | 1716150 B1 | 4/2008 |
| EP | 1328289 B1 | 9/2008 |
| EP | 2103310 A8 | 12/2009 |
| EP | 2077998 B1 | 3/2011 |
| EP | 1857107 B1 | 4/2011 |
| EP | 2086973 B1 | 1/2012 |
| EP | 1663283 B1 | 5/2012 |
| EP | 2334674 B1 | 6/2012 |
| GR | 900100716 A | 1/1992 |
| JP | H1070418 A2 | 3/1998 |
| RU | 2147250 C1 | 4/2000 |
| RU | 2189230 C1 | 9/2002 |
| RU | 2189790 C1 | 9/2002 |
| RU | 2226097 C2 | 3/2004 |
| RU | 2277412 C2 | 6/2006 |
| RU | 2326657 C1 | 6/2008 |
| UA | 7531 U | 6/2005 |
| UA | 13046 U | 3/2006 |
| UA | 21474 U | 3/2007 |
| WO | WO8903837 A1 | 5/1989 |
| WO | WO8909220 A1 | 10/1989 |
| WO | WO9105047 A1 | 4/1991 |
| WO | WO9208453 A1 | 5/1992 |
| WO | WO9211850 A2 | 7/1992 |
| WO | WO9218126 A1 | 10/1992 |
| WO | WO9310784 A1 | 6/1993 |
| WO | WO9409808 A1 | 5/1994 |
| WO | WO9501096 A1 | 1/1995 |
| WO | WO9510185 A1 | 4/1995 |
| WO | WO9528493 A1 | 10/1995 |
| WO | WO9531194 A1 | 11/1995 |
| WO | WO9602563 A1 | 2/1996 |
| WO | WO9618099 A1 | 6/1996 |
| WO | WO9618745 A1 | 6/1996 |
| WO | WO9620276 A1 | 7/1996 |
| WO | WO9814606 A1 | 4/1998 |
| WO | WO9823267 A1 | 6/1998 |
| WO | WO9845466 A1 | 10/1998 |
| WO | WO9906397 A2 | 2/1999 |
| WO | WO9906410 A1 | 2/1999 |
| WO | WO9915635 A1 | 4/1999 |
| WO | WO9932637 A1 | 7/1999 |
| WO | WO9935255 A2 | 7/1999 |
| WO | WO9943336 A1 | 9/1999 |
| WO | WO9946367 A2 | 9/1999 |
| WO | WO0015800 A3 | 3/2000 |
| WO | WO0062778 A1 | 10/2000 |
| WO | WO0142219 A2 | 6/2001 |
| WO | WO0177075 A2 | 10/2001 |
| WO | WO0189520 A2 | 11/2001 |
| WO | WO0218395 A1 | 3/2002 |
| WO | WO0229001 A2 | 4/2002 |
| WO | WO02055536 A2 | 7/2002 |
| WO | WO02066494 A2 | 8/2002 |
| WO | WO03044021 A2 | 5/2003 |
| WO | WO03097056 A1 | 11/2003 |
| WO | WO03099808 A1 | 12/2003 |
| WO | WO03103661 A1 | 12/2003 |
| WO | WO04018460 A1 | 3/2004 |
| WO | WO04022055 A1 | 3/2004 |
| WO | WO04089381 A1 | 10/2004 |
| WO | WO04094379 A2 | 11/2004 |
| WO | WO04105484 A1 | 12/2004 |
| WO | WO05012286 A1 | 2/2005 |
| WO | WO05019202 A1 | 3/2005 |
| WO | WO05070932 A2 | 8/2005 |
| WO | WO05107871 A2 | 11/2005 |
| WO | WO05110416 A2 | 11/2005 |
| WO | WO05110991 A1 | 11/2005 |
| WO | WO06004589 A2 | 1/2006 |
| WO | WO06004702 A1 | 1/2006 |
| WO | WO06010628 A1 | 2/2006 |
| WO | WO06019187 A1 | 2/2006 |
| WO | WO06037117 A1 | 4/2006 |
| WO | WO06069258 A1 | 6/2006 |
| WO | WO2006094187 A2 | 9/2006 |
| WO | WO2007005990 A3 | 1/2007 |
| WO | WO2007022380 A2 | 2/2007 |
| WO | WO2007114827 A1 | 10/2007 |
| WO | WO2007120621 A2 | 10/2007 |
| WO | WO2007124181 A2 | 11/2007 |
| WO | WO2007128866 A1 | 11/2007 |
| WO | WO2008011032 A1 | 1/2008 |
| WO | WO2008030466 A1 | 3/2008 |
| WO | WO2008045393 A2 | 4/2008 |
| WO | WO2008136948 A1 | 11/2008 |
| WO | WO2008137176 A1 | 11/2008 |
| WO | WO2008154251 A2 | 12/2008 |
| WO | WO2008156699 A1 | 12/2008 |

(56) References Cited

FOREIGN PATENT DOCUMENTS

| | | |
|---|---|---|
| WO | WO2009038784 A1 | 3/2009 |
| WO | WO2009055033 A1 | 4/2009 |
| WO | WO2009078992 A1 | 6/2009 |
| WO | WO2009105044 A1 | 8/2009 |
| WO | WO2009115548 A3 | 9/2009 |
| WO | WO2009117156 A1 | 9/2009 |
| WO | WO2010025201 A1 | 3/2010 |
| WO | WO2010025202 A1 | 3/2010 |
| WO | WO2010042646 A1 | 4/2010 |
| WO | WO2010042649 A2 | 4/2010 |
| WO | WO2010065882 A1 | 6/2010 |
| WO | WO2010132657 A1 | 11/2010 |
| WO | WO2010147621 A1 | 12/2010 |
| WO | WO2010150100 A1 | 12/2010 |
| WO | WO2011002760 A1 | 1/2011 |
| WO | WO2011008534 A1 | 1/2011 |
| WO | WO2011022056 A2 | 2/2011 |
| WO | WO2011091723 A1 | 8/2011 |
| WO | WO2011136813 A1 | 11/2011 |
| WO | WO2011136815 A1 | 11/2011 |
| WO | WO2012042023 A2 | 4/2012 |
| WO | WO2013082458 A1 | 6/2013 |

OTHER PUBLICATIONS

Beyersdorf, et al. (2009) "Controlled reperfusion after acute and persistent limb ischemian" *Seminars Vascular Surgery*, 22(1): 52-57.

Biberthaler et al. (2001) "The Influence of Organ Temperature on Hepatic Ischemia-Reperfusion Injury: A Systematic Analysis1" *Transplantation*, 72(9): 1486-1490.

Busuttil et al. (2011) "rPSGL-Ig for Improvement of Early Liver Allograft Function: A Double-Blind, Placebo-Controlled, Single-Center Phase II Study" *Am. J. Transplant*, 11: 786-797.

Castella et al. (2003) "A new role for cardioplegic buffering: should acidosis or calcium accumulation be counteracted to salvage jeopardized hearts?" *J. Thorac. Cardiovasc. Surg.*, 126(5): 1442-1448.

De Fraga et al. (2011) "Fructose 1-6 bisphosphate versus University of Wisconsin solution for rat liver preservation: does FBP prevent early mitochondrial injury?" *Transplant Proc.*, 43: 1468-1473.

Fondevila et al. (2009) "Cytoprotective Effects of a Cyclic RGD Peptide in Steatotic Liver Cold Ischemia and Reperfusion Injury" *Am. J. Transplant*, 9: 2240-2250.

Fortner et al. (1974) "Major hepatic resection using vascular isolation and hypothermic perfusion." *Ann. Surg.*, 180(4): 644-652.

Fruhauf et al. (2004) "Feasibility of Veno-Venous Bypass Surgery Using Leukocyte Adhesion Filters during Abdominal Surgery in a Porcine Model" *Eur. Surg. Res.*, 36: 83-87.

Fukuhiro et al. (2000) "Cardioplegic strategies for calcium control—Low Ca2+, high Mg2+, citrate, or Na+/H+ exchange inhibitor HOE-642" *Circulation*, 2[suppl III]:III-319-III-325.

Gerwig et al. (2002) "Prevention of Ischemia-Reperfusion Injury in the Rat Liver by Atrial Natriuretic Peptide: Insights into Mechanisms and Mode of Cell Death." *University, Diss., München*, 122 pages.

Ghomeshi et al. (1998) "The Effects of Exogenous L-Aspartate and L-Glutamate Du Ring Ischemia-Reperfusion for Cardiac Surgery.—A Magnetic Resonance Study in Isolated Pig Hearts." *Thesis, Master of Science, University of Manitoba*, 146 pages.

Gopalan et al. (1997) "Neutrophil CD18-dependent arrest on intercellular adhesion molecule 1 (ICAM-1) in shear flow can be activated through L-selectin." *J. Immunol.*, 158: 367-375.

Halldorsson et al. (2000) "Lowering reperfusion pressure reduces the injury after pulmonary ischemia." *Ann. Thorac. Surg.*, 69(1): 198-203.

Hannoun et al. (1996) "Major extended hepatic resections in diseased livers using hypothermic protection: preliminary results from the first 12 patients treated with this new technique." *J. Am. Coll. Surg.*, 183: 597-605 [Abstract Only].

Heijnen et al. (2003) "Decrease in core liver temperature with 10° C. by in situ hypothermic perfusion under total hepatic vascular exclusion reduces liver ischemia and reperfusion injury during partial hepatectomy in pigs" *Surgery*, 134: 806-817.

Jaeschke et al. (2006) "Role of neutrophils in acute inflammatory liver injury" *Liver Int.*, 26(8): 912-919.

Kaakinen et al. (2008) "Approaches to Improving Brain Protection in Cardiac and Aortic Surgery." *University, Diss., München*, 122 pages.

Kronon, et al. (2000) "Reducing post ischemic reperfusion damage in neonates using a terminal warm substrate-enriched blood cardioplegic reperfusate" *Ann. Thorac. Surg.*, 70(3): 765-770.

Leverve (2007) "Mitochondrial function and substrate availability" *Crit. Care Med.*, 35(9): S454-460.

Lick, et al. (2000) "Technique of controlled reperfusion of the transplanted lung in humans" *Ann. Thorac. Surg.*, 69(3): 910-912.

Liedtke et al. (1976) "Effects of treatment with pyruvate and tromethamine in experimental myocardial ischemia." *Circulation Res.*, 39: 378-387.

Luciani et al. (2011) "Myocardial protection in heart transplantation using blood cardioplegia: 12-year outcome of a prospective randomized trial." *J. Heart Lung Transplant*, 30: 29-36.

McCord (1985) "Oxygen-derived free radicals in postischemic tissue injury." *N. Engl. J. Med.* 312(3): 159-163.

Ohkado et al. (1994) "Evaluation of Highly Buffered Low-Calcium Solution for Long-Term Preservation of the Heart Comparison with University of Wisconsin Solution" *TJ Thorac Cardiovasc Surg.*, 108:762-771; 11 pages.

Parks et al. (1983) "Role of oxygen free radicals in shock, ischemia, and organ preservation." *Surgery*, 94: 428-432.

Rothlein et al. (1986) "A human intercellular adhesion molecule (ICAM-1) distinct from LFA-1." *J. Immunol.*, 137: 1270-1274.

Sano et al. (1995) "Beneficial effect of fructose-1,6-bisphosphate on mitochondrial function during ischemia-reperfusion of rat liver" *Gastroenterology*, 108: 1785-1792.

Schnickel et al. (2006) "Modified reperfusion in clinical lung transplantation: The results of 100 consecutive cases" *J. Thorac. Cardiovasc. Surg.*, 131(1): 218-223.

Sheth et al. (2011) "Glycine maintains mitochondrial activity and bile composition following warm liver ischemia-reperfusion injury." *J. Gastroenterol. Hepatol.*, 26: 194-200.

Takeuchi et al. (1989) "Stabilizing effects of some amino acids on membranes of rabbit erythrocytes perturbed by chlorpromazine." *J. Pharm. Sci.*, 78(1): 3-7.

Wamser et al. (2003) "Detrimental effects of controlled reperfusion on renal function after porcine autotransplantation are fully compensated by the use of Carolina rinse solution" *Transplant Int.*, 16: 191-196.

Hong et al. (2012) "Regulated Hepatic Reperfusion Mitigates Ischemia-Reperfusion Injury and Improves Survival after Prolonged Liver Warm Ischemia: A Pilot Study on a Novel Concept of Organ Resuscitation in a Large Animal Model" *J Am Coll Surg*, 214:505-516.

\* cited by examiner

REPERFUSION PROTECTION SOLUTION AND USES THEREOF

CROSS-REFERENCE TO RELATED APPLICATIONS

This application is a 371 National Phase of PCT/US2012/067348, filed on Nov. 30, 2012, which claims benefit of and priority to U.S. Ser. No. 61/566,419, filed on Dec. 2, 2011, which is incorporated herein by reference in its entirety for all purposes.

STATEMENT OF GOVERNMENTAL SUPPORT

[Not Applicable]

BACKGROUND

Organs subject to various surgical procedures and/or organs for transplantation (grafts) often face a period of diminished or interrupted blood flow (e.g., during a surgical procedure, as a consequence of injury, or during removal and transit for transplants). Organ transplants, in particular, face a period of having to survive outside the donor and recipient. During that time, although grafts are preserved by cooling and other measures, they are short of blood supply (ischemia). Prolonged ischemia can be damaging because of lack of oxygen and nutrients. When the graft organ is attached to the blood circulation of the recipient, or when circulation is restored to an organ in a surgical procedure and/or as a consequence of repair to damage, the tissue is suddenly reperfused with blood (reperfusion). However, instead of restoring normal function, reperfusion can result in inflammation and additional damage to the organ, an event known as reperfusion injury. This type of reperfusion-related inflammation and cellular insult can further destroy an already damaged/ischemic graft. Depending on the severity of the initial ischemia, the tissue can subsequently be seriously or permanently damaged, subjecting the newly transplanted graft to an increased risk of graft dysfunction/failure and subsequent organ rejection from the recipient. The severe form of ischemia/reperfusion injury associated with solid organ transplantation is a life-threatening condition.

Ischemia and reperfusion injury (IRI) can occur during hepatic surgery with clamping of the vascular pedicle of the porta hepatis (Pringle Maneuver) and in liver transplantation (LT). Liver IRI has a profound clinical impact on graft function after LT when organs from marginal or extended criteria donors are used because its deleterious effects are augmented in these grafts (Merion et al. (2006) Ann. Surg., 244: 555-562; Cameron et al. (2006) Ann. Surg., 243: 748-753; Anderson et al. (2011) Liver Transpl., 17: 189-200). IRI causes up to 12% of early organ failure and 15% to 25% of long-term graft dysfunction (Hilmi et al. (2008) Liver Transpl., 14: 504-508). Post-reperfusion syndrome, with an incidence rate of up to 30%, causes acute cardiovascular collapse that may lead to death of the patients (Aggarwal et al. (1987) Transpl. Proc., 19: 54-55; Bukowicka et al. (2011) Ann. Transplant, 16: 26-30; Paugam-Burtz et al. (2009) Liver Transpl., 15: 522-529). Poor graft function after LT contributes to the need for retransplantation of the liver and results in an increase in resource utilization.

Hepatic IRI begins with an interruption of blood flow to the liver (ischemia) that leads to depletion of energy substrates and oxygen (Goto et al. (1992) Hepatology, 15: 432-437), acidosis, impaired adenosine triphosphate (ATP) regeneration (Karwinski et al. (1989) J. Surg. Res., 46: 99-103; Kamiike et al. (1985) Transplantation, 39: 50-55), and reduction of endogenous antioxidant glutathione (GSH) (Kurokawa et al. (1996) J. Surg. Res., 66: 1-5), and the reduced form of nicotine adenine dinucleotide (NADH), a key enzyme in the electron transport chain (Tomitsuka et al. (2010) Ann. N.Y. Acad. Sci., 1201: 44-49; Siegel et al. (2011) Acta. Physiol. (Oxf), 203: 225-234). Furthermore, ischemia also results in calcium influx across the plasma membrane and breakdown of the plasma membrane barrier (Kurita et al. (1993) J. Hepatol., 18: 196-204; Uchida et al. (1994) J. Hepatol., 20: 714-719). Paradoxically, the return of blood flow after a period of ischemia (reperfusion) results in induced oxidative stress and further hepatocyte injury through a complex cascade of events that include the infiltration of activated neutrophils in hepatic endothelial cells and systemic release of inflammatory mediators, reactive oxygen species (ROS) and proteases (Weiss (1989) N. Engl. J. Med., 320: 365-376). This state of cellular metabolic debt, in addition to other immunological and inflammatory mediators, result in the activation of the mitochondrial permeability transition (MPT), a key process in this lethal cell injury, leading to mitochondrial swelling, depolarization, uncoupling, plasma membrane rupture, and subsequent cell death (Weiss (1989) N. Engl. J. Med., 320: 365-376; Jaeschke (2000) J. Gastroenterol. Hepatol., 15: 718-724; Kim et al. (2003) Curr. Mol. Med., 3: 527-535; Nishimura (1998) Hepatology, 27: 1039-1049). The ability of the cell to recover from this type ischemic insult is dependent upon the energy state of the cell prior to organ reperfusion. While a brief period of warm ischemia (WI) may not cause significant alteration in the energy reserve of the mitochondria, prolonged WI results in a state of severe cellular metabolic deficit, an increased in toxic metabolites present in the host splanchnic venous blood, and an elevated portal reperfusion pressure that further predispose the compromised hepatocytes to reperfusion injury.

SUMMARY

It was a surprising discovery that replenishing energy substrates and providing a nurturing milieu for cellular recovery prior to exposure of host blood, which contains toxic metabolites from the stagnation of splanchnic circulation and elevated reperfusion pressure, would mitigate the adverse effects of IRI. In various embodiments the novel therapeutic strategy of regulated hepatic reperfusion (RHR) delivers a substrate-enriched, oxygen-saturated, and leukocyte depleted perfusate under regulated reperfusion pressure during the critical initial period of organ revascularization.

In certain embodiments an organ reperfusion protection solution is provided. In various embodiments the solution comprises a buffer (e.g., a physiologically compatible buffer), one or more substrates for the synthesis of adenosine triphosphate (ATP) under anaerobic conditions, citrate-phosphate-dextrose (CPD); and one or more amino acids that stabilize cell membranes. In certain embodiments the pH of the solution ranges from about 7.8 to about 8.6.

In certain embodiments an organ reperfusion protection solution is provided where the solution comprises a buffer (e.g., a physiologically compatible buffer); one or more substrates for the synthesis of adenosine triphosphate (ATP) under anaerobic conditions; citrate-phosphate-dextrose (CPD); and one or more amino acids that stabilize cell membranes; where the pH of the organ reperfusion protection solution ranges from about pH 7.5 to about pH 8.8. In certain embodiments the pH of the solution ranges from about pH 8.1 to about pH 8.4. In certain embodiments the pH of the solution is about pH 8.4. In certain embodiments the buffer comprises a material selected from the group consisting of sodium bicarbonate, tromethamine, tham, and dichloroacetate. In certain embodiments the buffer comprises tromethamine. In certain embodiments the one or more substrates for the synthesis of ATP comprise aspartate and/or glutamate. In certain embodiments the one or more amino acids that stabilize cell membranes comprise one or more amino acids selected from the group consisting of glycine, lycine, and aspartic acid. In certain embodiments the one or more amino acids comprises glycine. In certain embodiments the solution comprises: citrate, phosphate, dextrose (CPD); D-fructose-1,6-biphosphate; glycine; 1-monosodium glutamate; 1-monosodium aspartate; magnesium sulfate; and tromethamine.

In certain embodiments the organ reperfusion protection solution comprises: magnesium sulfate; tromethamine; citric acid; sodium citrate; sodium phosphate; D-fructose-1,6-bisphosphate; dextrose; L-monosodium glutamate; L-monosodium aspartate; glycine; and sterile water or normal saline. In some embodiments, the sterile water or normal saline is normal saline. In some embodiments, the sterile water or normal saline is sterile water.

In certain embodiments the organ reperfusion protection solution comprises: magnesium sulfate; tromethamine; citric acid; sodium citrate; sodium phosphate; D-fructose-1,6-bisphosphate; dextrose; L-monosodium glutamate; L-monosodium aspartate; glycine; glacial acetic acid; and sterile water or normal saline. In some embodiments, the sterile water or normal saline is normal saline. In some embodiments, the sterile water or normal saline is sterile water.

In certain embodiments the organ reperfusion protection solution comprises: magnesium sulfate; tromethamine; citric acid monohydrate; sodium citrate dihydrate; sodium phosphate monobasic, monohydrate; D-fructose-1,6-bisphosphate trisodium salt, octahydrate; dextrose, anhydrous; L-monosodium glutamate, monohydrate; L-monosodium aspartate, monohydrate; glycine; and sterile water or normal saline. In some embodiments, the sterile water or normal saline is normal saline. In some embodiments, the sterile water or normal saline is sterile water.

In certain embodiments the organ reperfusion protection solution comprises: magnesium sulfate; tromethamine; citric acid monohydrate; sodium citrate dihydrate; sodium phosphate monobasic, monohydrate; D-fructose-1,6-bisphosphate trisodium salt, octahydrate; dextrose, anhydrous; L-monosodium glutamate, monohydrate; L-monosodium aspartate, monohydrate; glycine; glacial acetic acid; and sterile water or normal saline. In some embodiments, the sterile water or normal saline is normal saline. In some embodiments, the sterile water or normal saline is sterile water.

In certain embodiments the magnesium sulfate ranges from about 10 g to about 14 g per liter of solution. In certain embodiments the tromethamine ranges from about 7 g to about 9 g per liter of solution. In certain embodiments the citric acid ranges from about 0.5 g to about 1.0 g per liter of solution. In certain embodiments the sodium citrate ranges from about 5 g to about 7 g per liter of solution. In certain embodiments the sodium phosphate ranges from about 0.25 g to about 0.75 g per liter of solution. In certain embodiments the the D-fructose-1,6-bisphosphate ranges from about 4 g to about 8 g per liter of solution. In certain embodiments the L-monosodium glutamate ranges from about 8 g to about 12 g per liter of solution. In certain embodiments the L-monosodium aspartate ranges from about 8 g to about 12 g per liter of solution. In certain embodiments the glycine ranges from about 0.2 g to about 0.6 g per liter of solution. In certain embodiments, where glacial acetic acid is present the glacial acetic acid ranges from about 0.5 mL to about 1.5 mL per liter of solution. In certain embodiments a liter of solution comprises: about 12.01 g magnesium sulfate; about 8.1 g tromethamine; about 0.73 g citric acid; about 5.91 g sodium citrate; about 0.49 g sodium phosphate; about 5.50 g D-fructose-1,6-bisphosphate; about 5.22 g dextrose; about 10.7 g 1-monosodium glutamate; about 9.8 g 1-monosodium aspartate; about 0.36 g glycine; and sterile water, q.s. 1,000 mL. In certain embodiments a liter of solution, the solution comprises: about 12.01 g magnesium sulfate; about 8.1 g tromethamine; about 0.73 g citric acid; about 5.91 g sodium citrate; about 0.49 g sodium phosphate; about 5.50 g D-fructose-1,6-bisphosphate; about 5.22 g dextrose; about 10.7 g 1-monosodium glutamate; about 9.8 g 1-monosodium aspartate; about 0.36 g glycine; 0.9 mL glacial acetic acid, and sterile water, q.s. 1,000 mL. In certain embodiments the pH of the solution is about 8.4. In certain embodiments the solution is sterile. In certain embodiments the solution is mixed with whole blood (or a blood fraction or synthetic blood). In certain embodiments the ratio of blood to solution ranges from about 1:1 to about 10:1. In certain embodiments the ratio of blood to solution ranges from about 2:1 to about 6:1. In certain embodiments the ratio of blood to solution is about 4:1. In certain embodiments leukocytes in the mixed solution are reduced or are substantially removed. In certain embodiments the solution is oxygenated (e.g., oxygenated to maintain oxygen saturation at about 100%). In certain embodiments the solution is heated (e.g., to a temperature ranging from about 25° C. to about 37° C., or to a temperature ranging from about 26° C. to about 36° C., or to a temperature ranging from about 30° C. to about 34° C.; or to a temperature ranging from about 30° C. to about 32° C.).

In various embodiments methods of mitigating ischemic reperfusion injury in a solid organ of a mammal are provided where the methods comprise contacting the solid organ with an organ reperfusion protection solution as described and/or as claimed herein. In certain embodiments the contacting comprises reperfusing the organ with a perfusate comprising a reperfusion protection solution described and/or claimed herein. In certain embodiments the reperfusion protection solution is combined with whole blood (or with a blood fraction or with synthetic blood). In certain embodiments the ratio of blood to the reperfusion protection solution ranges from about 1:1 to about 10:1. In certain embodiments the ratio of blood to the reperfusion solution is about 4:1. In certain embodiments the perfusate is oxygenated before or during delivery to the organ. In certain embodiments the perfusate is oxygenated to 100% oxygen saturation. In certain embodiments leukocytes are reduced or eliminated from the perfusate before the perfusate is delivered to the organ. In certain embodiments the leukocytes are reduced or eliminated using a leukocyte reduction filter. In certain embodiments the perfusate is delivered under a regulated pressure (e.g., a pressure ranging from about 2 mm Hg to about 24 mm Hg, or a pressure ranging from about 8 mm Hg to about 12 mm Hg). In certain embodiments the perfusate is delivered under a regulated pressure corresponding to a physiological pressure for that mammal and organ. In certain embodiments the perfusate is at a temperature below normal body temperature of the mammal. In certain embodiments the perfusate is at a temperature ranging from about 26° C. to about 35° C. or at a temperature ranging from about 30° C. to about 32° C. In certain embodiments the reperfusion is performed at the normal body temperature of the mammal. In certain embodiments the method is performed for a period ranging from about 10 min up to 2 hrs, or from about 20 minutes up to about 1 hr, or from about 30 minutes to about 40 minutes. In certain embodiments the organ is selected from the group consisting of a liver, a kidney, a pancreas, a spleen, heart, lungs, skin, an intestine, a composite tissue such as limbs or extremities. In certain embodiments the organ is a liver. In certain embodiments the organ is a transplant organ. In certain embodiments the organ is an organ in a subject where the organ is subject to a period of reduced or no blood supply. In certain embodiments the organ is subjected to a period of reduced or no blood flow in a surgical procedure. In certain embodiments the organ is subjected to a period of reduced or no blood flow as a consequence of an injury. In certain embodiments the method is performed as a part of a surgical procedure. In certain embodiments the method is performed before implanting the organ into the mammal. In certain embodiments the mammal is a human. In certain embodiments the mammal is a non-human mammal.

In certain embodiments methods of transporting an organ from a mammal are provided where the methods comprise contacting the organ with a reperfusion protection solution optionally in a regulated reperfusion protocol (e.g., an RHR) as described and/or claimed herein where the contacting/reperfusing is performed during or after transport of the organ.

In certain embodiments methods of protecting an organ from reperfusion injury are provided where the methods comprise contacting the organ with a reperfusion protection solution optionally in a regulated reperfusion protocol (e.g., an RHR) as described and/or claimed herein where the contacting/reperfusing is performed before exposing the organ to recipient blood.

In certain embodiments methods of protecting an organ subject to transient ischemia in vivo from reperfusion injury are provided where the methods comprise contacting the organ with a reperfusion protection solution optionally in a regulated reperfusion protocol (e.g., an RHR) as described and/or claimed herein before re-exposing the organ the host blood supply.

Definitions

The terms "perfusate" refers to the solution that is used to reperfuse the organ(s) of interest prior to (or during) revascuarlization with host blood. In certain embodiments the perfusate comprises the reperfusion protection solution described herein. In certain embodiments the perfusate comprises a mixture of the reperfusion protection solution and whole blood or a blood fraction or a synthetic blood substitute.

The term "subject" or "mammal" are intended to include both humans and non-human mammals. Thus, in certain embodiments, subjects or mammals include, but are not limited to humans, non-human primates, canines, equines, felines, porcines, ungulates, lagomorphs, and the like.

The following abbreviations are used in this example: IRI: ischemia and reperfusion injury; RHR: regulated hepatic reperfusion; WI: warm ischemia; LT: liver transplantation; PRS: post-reperfusion syndrome; and ETC: electron transport chain.

DETAILED DESCRIPTION

Figure 1:
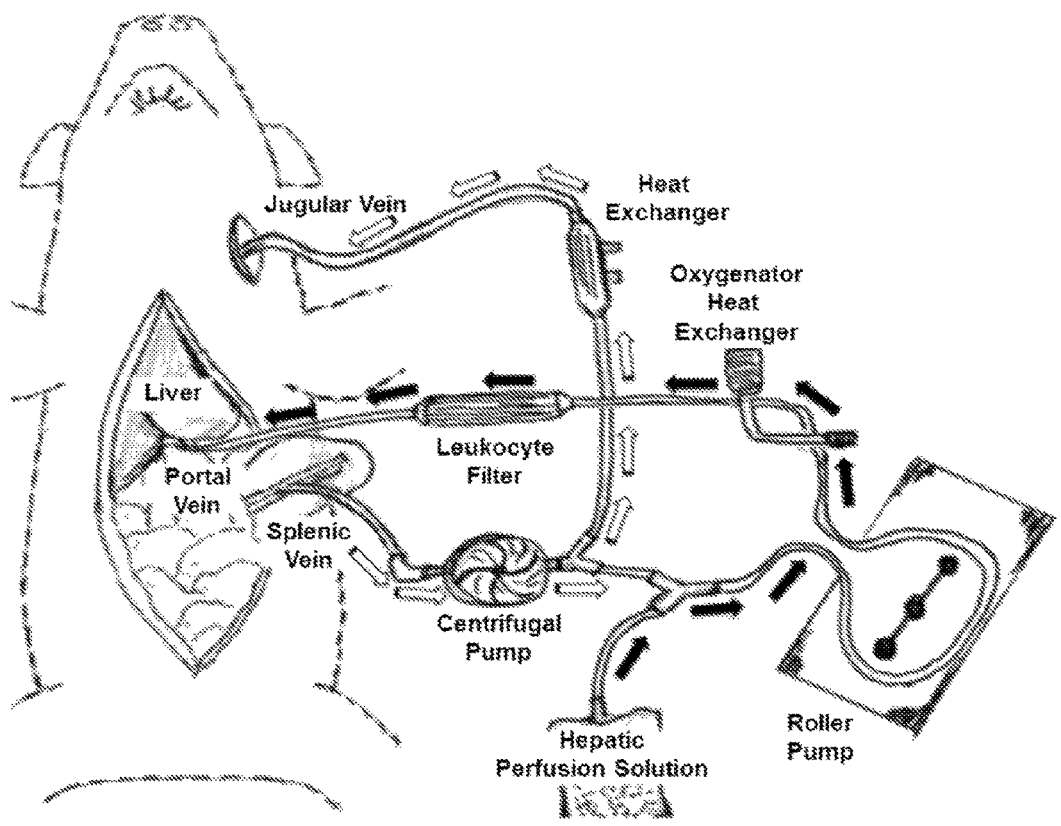
FIG. 1 schematically illustrates regulated hepatic reperfusion (RHR) and splenojugular venovenous bypass circuits. An extracorporeal centrifugal pump recirculates the animal's splanchnic venous blood to the heart through a splenojugular venovenous bypass (direction of blood flow shown by white arrows) to avoid congestion of the splanchnic circulation during total portal occlusion (hepatic WI). During RHR, an amount of the animal's splanchnic venous blood is diverted through a Y-connector from the centrifugal pump and mixed with hepatic perfusion solution (H solution) in a 4:1 dilution ratio (perfusate). Another extracorporeal roller pump recirculates the perfusate through a pediatric oxygenator-heat exchanger and leukoreduction filter before perfusion of the liver through the portal vein (direction of perfusate flow shown by black arrows). The roller pump regulates the reperfusion pressure between 8 and 12 mmHg and the oxygenator/heat exchanger unit maintains the perfusate oxygen saturation to 100% and temperature at 30° C. to 32° C.

In various embodiments a reperfusion protection solution is provided that mitigates or prevents reperfusion injury in an organ subject to an ischemic event (e.g., resection, transplantation, marginal transplantation, graft, etc.). The use of such a solution to mitigate or prevent reperfusion injury in such an organ is also provided.

The solution can be used to protect transplant organs from reperfusion injury after removal and/or during transport, and/or prior to re-implantation. The solution is also useful to protect marginal transplants and grafts from reperfusion injury. In addition, the solution can be used in vivo to protect organs subjected to a transient ischemic event (e.g., during surgery and/or as a consequence of injury) from reperfusion injury.

It was a surprising discovery that use of the reperfusion protection solution(s) described herein, particularly in combination with a regulated reperfusion regime (e.g., regulating pressure, temperature, oxygen saturation of the perfusate) can substantially reduce mortality due to reperfusion injury. While in certain embodiments, the reperfusion protection solution can be used alone, in certain embodiments, the solution is combined with whole blood or with a blood faction or with synthetic blood before being contacted with (reperfused into) the subject organ. In various embodiments the perfusate is depleted (wholly or partially) of leukocytes prior to administration to the subject organ.

The methods and reperfusion protection solution described herein can be used with any of a number of organs. Such organs include, but are not limited to group consisting of a liver, a kidney, a pancreas, a spleen, heart, lungs, skin, intestine, and the like. In certain embodiments the organs include composite tissues. In certain embodiments the solutions and methods described herein are particular well suited to protect liver from reperfusion injury.

The methods and reperfusion protection solutions described herein can also be used for the protection of composite tissues from reperfusion injury following their transportation and/or prior to attachment or reattachment. Such composite tissues include, but are not limited to, skin, bone, nerves, and the extremities. Illustrative, but non limiting examples of composited tissues include, but are not limited to limbs and extremities (e.g., arms, legs, feet, hands, fingers, toes, noses, ears, and the like).

Reperfusion Protection Solutions.

In certain embodiments the reperfusion protection solution comprises a buffer; one or more substrates for the synthesis of adenosine triphosphate (ATP) under anaerobic conditions; citrate-phosphate-dextrose (CPD); and one or more amino acids that stabilize cell membranes. In various embodiments the reperfusion protection solution is formulated with a buffer to facilitate regulation of the solution pH. In certain embodiments the pH of the organ reperfusion protection solution typically ranges from about pH 7.8 to about pH 8.6, more preferably from about pH 7.9 or from about pH 8.0 up to about pH 8.6 or up to about pH 8.5, still more preferably from about pH 8.1 up to about pH 8.4.

Any of a number of physiologically compatible buffers can be used in the reperfusion solutions contemplated herein. Illustrative, but non-limiting examples of buffers include buffers comprising sodium bicarbonate, and/or tromethamine, and/or tham, and/or dichloroacetate. In certain embodiments the buffer comprises tromethamine.

In various embodiments any one or more of a number of substrates for the synthesis of ATP can be incorporated into the reperfusion protection solution. Such substrates are well known to those of skill in the art and include, but are not limited to aspartate and/or glutamate.

In various embodiments the one or more amino acids that stabilize cell membranes comprise one or more amino acids selected from the group consisting of glycine, lycine, and aspartic acid. However the use of other "protective/stabilizing" naturally occurring (or modified) amino acids is also contemplated. In certain embodiments the one or more amino acids comprises glycine.

One illustrative formulation, particularly well-suited for reperfusion of hepatic tissue (but not limited to use in hepatic tissues) is shown in Table 1. Without being bound by a particular theory, the proposed action of each of the components is also summarized in Table 1

TABLE 1

Illustrative composition of reperfusion solution (H solution).

| Ingredients | Proposed Actions |
|---|---|
| Citrate, phosphate, dextrose (CPD) | Reduce concentration of ionized calcium |
| D-fructose-1,6-biphosphate | Preserves the oxidative phosphorylation capacity of hepatic mitochondria substrates for glycolysis |
| Glycine | Stabilizes cell membrane and inhibits inflammatory cytokines |
| L-monosodium glutamate | A substrate for adenosine triphosphate production during anaerobic state |
| L-monosodium aspartate | A substrate for adenosine triphosphate production during anaerobic state |
| Magnesium sulfate | Reduces concentration of ionized calcium |
| Tromomethamine | Buffers the acidotic cellular medium |

The formulation(s) can be prepared simply by combining the various components into a solution according to methods well known to those of skill in the art. In certain embodiments the formulation is assembled from sterile components. Alternatively, or additionally, the reperfusion solution can be sterilized (e.g., in an autoclave).

Illustrative formulation parameters for a reperfusion protection solution are illustrated in Table 2. It will be recognized that these parameters are illustrative and not limiting. Various equivalents, or substantial equivalents, for the components listed in Tables 1 and/or 2 will be known to one of skill in the art. In certain embodiments it is contemplated that the various ranges, range endpoints, or values described herein can be varied by up to 30%, or 20%, or 10%, or 5%, or 3%, or 2%, or 1%. In certain embodiments one or more of the components listed in Table 1 and/or 2 can be omitted from the reperfusion protection solution formulation.

TABLE 2

Illustrative formulation parameters for one liter of reperfusion protection solution (H solution) (pH 8.4).

| Component | Typical Range | Illustrative Formulation |
|---|---|---|
| tromethamine | 7 to 9 g | 8.1 g |
| magnesium sulfate | 10 to 14 g | 12.01 g |
| citric acid, monohydrate, granular | 0.5 to 1 g | 0.74 g |
| sodium citrate, dihydrate, granular | 5 to 7 g | 5.9 g |
| sodium phosphate monobasic, monohydrate, granular | 0.25 g to 0.75 g | 0.5 g |
| D-fructose-1,6-bisphosphate trisodium salt, octahydrate | 4 g to 8 g | 5.5 g |
| dextrose, anhydrous | 3 g to 7 g | 5.2 g |
| L-monosodium glutamate, monohydrate | 8 g to 12 g | 10.7 g |
| L-monosodium aspartate, monohydrate | 8 g to 12 g | 9.8 g |
| glycine | 0.2 g to 0.6 g | 0.36 g |
| sterile water | | q.s. 1,000 mL |

These formulations are intended to be illustrative and not limiting. Using the teaching provided herein other variant reperfusion protection solutions can be prepared by one of skill in the art, and optionally optimized for use with particular organs.

Use of Reperfusion Protection Solution.

In various embodiments it is contemplated that the reperfusion solutions described herein can be used to reduce the injury to a tissue (particularly to a solid organ such as a liver, a kidney, a pancreas, a spleen, heart, lungs, skin, intestine, and the like or to various composite tissues, and the like). In various embodiments the reperfusion solutions can be used in a regulated reperfusion protocol (e.g., a protocol regulating pressure and/or temperature, and/or oxygen saturation of the reperfusate). In certain embodiments the reperfusion solutions are used in an RHR protocol.

In certain embodiments the reperfusion protection solutions alone (or in combination with blood, a blood fraction, and/or a synthetic blood) can be used to perfuse a transplant organ during removal, and/or transport, and/or during or after implantation. In certain embodiments the reperfusion protection solutions alone (or in combination with blood, a blood fraction, and/or a synthetic blood) can be used to reperfuse an organ in a subject where the organ has been denied blood flow or subject to reduced circulation for a period of time. Such reduced (or eliminated) circulation can, for example, be due to vascular occlusion during a surgical procedure or a consequence of an injury and/or cardiac failure. The methods described herein are contemplated to be of use in these and many other contexts.

In certain embodiments the reperfusion protection solution is utilized in a regulated reperfusion protocol (e.g., a regulated hepatic reperfusion (RHR)). Accordingly, in certain embodiments, a solid organ of a mammal (e.g., a liver) is reperfused with a perfusate comprising a reperfusion protection solution described herein. In certain embodiments the solution is used alone for reperfusion, while in other embodiments the reperfusion solution is combined with whole blood, a blood fraction, or synthetic blood. In certain embodiments the ratio of whole blood, blood fraction, or synthetic blood to reperfusion protection solution ranges from about 1:1 to about 10:1. In certain embodiments the ratio of whole blood, blood fraction, or synthetic blood to reperfusion protection solution ranges from about 2:1 to about 8:1 or from about 3:1 to about 6:1, or is about 4:1. In certain embodiments, particularly where the perfusate includes whole blood or certain blood fractions, leukocytes in the perfusate are reduced or eliminated. For example, in certain embodiments, the leukocytes can be reduced or eliminated using a leukocyte reduction filter.

In various embodiments the regulated reperfusion protocol involves regulating oxygen content of the perfusate. For example, in certain embodiments, the perfusate can be oxygenated. Thus, reperfusion protection solution according to any one of claims 1-31, wherein said solution is oxygenated. In certain embodiments the perfusate is oxygenated to maintain oxygen saturation at about 100%.

In various embodiments the regulated reperfusion protocol involves controlling/regulating the pressure at which the perfusate is delivered to the organ being reperfused. In certain embodiments the regulated pressure ranges from about 1 mm Hg, or from about 2 mm Hg up to about 30 mm Hg, or up to about 24 mm Hg. In certain embodiments the regulated pressure ranges from about 4 mm Hg up to about 20 mm Hg, or from about 6 mm Hg up to about 15 mm Hg, or from about 8 mm Hg up to about 12 mm Hg.

In various embodiments the regulated reperfusion protocol involves controlling/regulating the temperature of the perfusate delivered to the organ. While in some embodiments, the perfusate is maintained and/or delivered at body temperature for the particular mammal, in other embodiments, the perfusate is maintained and/or delivered at a temperature below normal body temperature of the mammal. In certain embodiments the perfusate is at a temperature ranging from about 26° C. up to about 35° C., or from about 28° C. up to about 34° C., or from about 30° C. up to about 32° C.

In various embodiments the regulated reperfusion protocol is performed for a period of time ranging from about 5 minutes or from about 10 minutes up to about 3 hours or up to about 2 hours. In certain embodiments the period of time ranges from about 20 minutes up to about 1 hr, or from about 30 minutes up to about 40 minutes.

In various embodiments the reperfusion protection solutions described herein can be used in a method of transporting an organ from a subject for transplantation into another subject. In certain embodiments organ(s) of interest are perfused with a perfusate comprising a reperfusion protection solution as described herein. In certain embodiments the organ(s) of interest are subjected to a regulated reperfusion protocol (e.g., as described above and in the Examples provided herein) during or after transport.

In various embodiments the reperfusion protection solutions described herein can be used to protect an organ subject to transient ischemia (e.g. ischemia due to injury or due to a surgical procedure) in vivo from reperfusion injury. In certain embodiments the ischemic organ(s) are perfused with a perfusate comprising a reperfusion protection solution as described herein. In certain embodiments the ischemic organ(s) are subjected to a regulated reperfusion protocol (e.g., as described above and in the Examples provided herein) before (or during) re-exposure of the organ(s) to the host blood supply.

The foregoing methods and the methods shown herein in the Examples are intended to be illustrative and not limiting. Using the teachings provided herein numerous other uses of the reperfusion protection solutions described herein and numerous variations of the depicted protocols will be available to one of skill in the art and are routinely optimized for use with a particular organ or organ system.

While the methods described herein are described with respect to use in humans, they are also suitable for animal, e.g., veterinary use. Thus certain preferred organisms include, but are not limited to humans, non-human primates, canines, equines, felines, porcines, ungulates, lagomorphs, and the like.

EXAMPLES

The following examples are offered to illustrate, but not to limit the claimed invention.

Example 1

Regulated Hepatic Reperfusion Mitigates Ischemia-Reperfusion Injury and Improves Survival after a Prolonged Liver Warm Ischemia: A Pilot Study on a Novel Concept of Organ Resuscitation in a Large Animal Model Ischemia-reperfusion injury (IRI) can occur during hepatic surgery and transplantation. IRI causes hepatic mitochondrial and microcirculatory impairment, resulting in acute liver dysfunction and failure. A novel strategy of regulated hepatic reperfusion (RHR) described in this example is used to reverse the cellular metabolic deficit that incurred during organ ischemia. The approach utilizes a substrate-enriched, oxygen-saturated, and leukocyte depleted perfusate delivered under regulated reperfusion pressure, temperature and pH. The utility of RHR in mitigating IRI after a prolonged period of warm ischemia is described.

As described herein using a 2-hour liver WI swine model, two methods of liver reperfusion were compared. Control group (n=6) received conventional reperfusion with unmodified portal venous blood under unregulated reperfusion pressure, temperature, pH. The experimental group (n=6) received RHR. The effects of RHR on post-reperfusion hemodynamic changes, liver function and 7-day animal survival were analyzed.

As described herein, RHR resulted in 100% survival compared to 50% in the control group (p=0.05). Post-reperfusion syndrome was not observed in the RHR group whereas it occurred in 83% in the control. RHR resulted in lesser degree of change from baseline serum alanine aminotransferase levels (ALT), aspartate aminotransferase (AST), and lactate dehydrogenase (LDH) after reperfusion compared to the control group. While histopathological evaluation showed minimal ischemic changes in the RHR group, a significant degree of coagulative hepatocellular necrosis was observed in the control group. Regulated hepatic reperfusion mitigates IRI, facilitates liver function recovery and improves survival after a prolonged period hepatic warm ischemia. This novel strategy has applicability to clinical hepatic surgery and organ transplantation, particularly when marginal grafts are used.

Materials and Methods

Animals and Preparation

All animal care procedures were performed in accordance with the Principles of Laboratory Animal Care formulated by the National Society for Medical Research and the Guide for the Care and Use of Laboratory Animals prepared by the Institute of Laboratory Animal Resources and published by the National Institute of Health (NIH publication no. 86-23, revised 1996). The UCLA Chancellor's Animal Research Committee approved all protocols.

After anesthesia and endotracheal intubation, 12 Yorkshire-Duroc pigs, 35 to 40 kg, were mechanically ventilated with respirator settings adjusted to keep oxygen tension, carbon dioxide tension and pH values within normal range. General anesthesia was maintained by intravenous fentanyl (2-3 µg/kg) and isoflurane (0.6-1%). Cefazolin (1 gram) was given intravenously for surgical wound prophylaxis. All procedures were performed using standard aseptic techniques. The left carotid artery was cannulated for arterial pressure measurements and left jugular vein for the Swan-Ganz pulmonary artery catheter for continuous pulmonary arterial pressure monitoring. The right jugular vein was cannulated (10-12 F, Terumo) for venous return during veno-venous bypass. Following a midline laparotomy incision, the liver was dissected free from its suspensory ligaments, and the portal vein, hepatic artery and bile ducts were dissected and isolated. The splenic vein was cannulated (10-12 F, Terumo) for decompression of splanchnic circulation during portal vein occlusion and a splenectomy was performed. The portal and hepatic veins were also cannulated for venous pressure measurements and blood sampling.

Swine Model of Two-Hour Warm Liver Ischemia

After collection of baseline liver tissue samples, hemodynamic and biochemical data, the hepatic artery and portal vein were completely occluded for two hours using vascular clamps to induce WI of the liver. Systemic anticoagulation with heparin was initiated before placement of vascular clamps on the portal vein and hepatic artery and maintained until hepatic reperfusion. Heparin was administered intravenously with an initial bolus dose of 10 international units (IU) per kilogram (kg) with subsequent doses at 5 IU/kg to maintain an activated clotting time (ACT) between 180-220 seconds. Extracorporeal circulation was maintained for splanchnic venous decompression via an extracorporeal centrifugal pump (Biomedicus, Minneapolis, Minn., USA). After two hours of liver WI, the animal either received the conventional reperfusion method (Control group, n=6) or regulated hepatic reperfusion (Experimental group, n=6). Upon emergence from general anesthesia, the animals were cared for in the vivarium. Animals were observed for 7 days and daily clinical and biochemical measurements were obtained. On post-operative days 3 and 7, an open liver biopsy and measurements of systemic arterial, hepatic and portal venous pressures were performed under general anesthesia. After completion of the study period, the animals were euthanized under the guidelines and protocols approved by the UCLA Chancellor's Animal Research Committee.

Methods of Hepatic Post-Ischemia Reperfusion

Conventional Method (Control Group)

After two hours of total liver WI, the liver was revascularized with the animal's unmodified portal venous blood by removal of the portal vein clamp. Reperfusion conditions, i.e. perfusion pressure, temperature (37° C.), oxygen saturation of portal venous blood (<60%), were not regulated. Twenty minutes after portal venous reperfusion, the hepatic arterial clamp was released to allow arterial perfusion of the liver.

Regulated Hepatic Reperfusion Strategy (Experimental Group)

After two hours of liver WI in the experimental group, the reperfusion of host blood was delayed until after a 30-40 minute period of RHR. FIG. 1 shows the circuit set up for RHR and veno-venous bypass. The perfusate (600 cc) was composed of a 4:1 mixture of host whole blood to hepatic perfusion solution (H solution). The H solution (pH 8.34) contained the following composition per liter: tromethamine, 8.1 grams (g); magnesium sulfate, 12.01 g; citric acid, 0.74 g; sodium citrate, 5.9 g; sodium phosphate, 0.5 g; D-fructose-1,6-biphosphate (FBP) 5.5 g; dextrose, 5.2 g; L-monosodium glutamate, 10.7 g; L-monosodium aspartate, and 9.8 g; glycine 0.36 g. (Table 1). During RHR, an amount of the animal's splanchnic whole blood was diverted through a Y-connector from an extracorporeal centrifugal pump and mixed with the H solution.

Another extracorporeal roller pump (Sarns, Ann Arbor, Mich., USA) recirculated the perfusate through a pediatric oxygenator/heat exchanger (Terumo, Ann Arbor, Mich., USA) to maintain oxygen saturation of the perfusate to 100% and then through a high efficiency leukocyte reduction filter (PALL Corporation, Ann Arbor, Mich., USA) for leukoreduction prior to perfusion of the liver via the portal vein. The roller blood pump and heat exchanger regulated the reperfusion pressure between 8-12 mmHg and perfusate temperature 30° C. to 32° C., respectively. After completion of RHR, the portal vein was decannulated and portal venotomy repaired. The portal venous blood flow was re-established followed by hepatic arterialization 20 minutes later, as in the control group.

Survival Outcome and Hemodynamic Measures

The primary endpoint of the study was 7-day animal survival after post-ischemia reperfusion. Secondary outcome measures included the incidence of post-reperfusion syndrome, liver function, and histological assessment of liver parenchyma. Post-reperfusion syndrome (PRS) was defined as a decrease in mean arterial pressure (MAP) of >30% from baseline within 5 minutes of reperfusion of liver and lasting for at least 1 minute in duration, or various combinations of bradyarrhythmias, hypotension, decreased vascular resistance, increased cardiac filling pressures with high pulmonary arterial pressures (Aggarwal et al. (1987) *Transpl. Proc.,* 19: 54-55).

Assessment of Hepatocellular Damage

Serum alanine aminotransferase (ALT), aspartate aminotransferase (AST), and lactate dehydrogenase (LDH) were measured at baseline (prior to liver WI), at the end of the 2-hour WI period, at 15 minutes interval during the first 2 hours after reperfusion and daily until post-operative day 7. An auto analyzer by ANTECH Diagnostics (Los Angeles) was used to measure the blood chemistry tests.

Myeloperoxidase (MPO) Assay

MPO is a naturally occurring constituent of neutrophils and is frequently used as a marker for neutrophil infiltration in hepatic tissue (Kato et al. (2000) *Am. J. Pathol.,* 157: 297-302). Frozen tissue was thawed and suspended in iced 0.5% hexadecyltrimethylammonium and 50 mmol potassium phosphate buffer solution (Sigma, St. Louis, Mo., USA), of pH 5. After samples were homogenized and centrifuged, 0.1 mL of the supernatant was mixed in the solution of hydrogen peroxide-sodium acetate and tetramethyl benzidine (Sigma, St. Louis, Mo., USA) One unit of myeloperoxidase activity was defined as the quantity of enzyme that degraded 1 μmol peroxide per minute at 25° C. per gram of tissue.

Histology

Liver tissue biopsy was obtained at baseline (prior to liver WI), at the end of the 2-hour WI period, 2-hour post-reperfusion, and post-operative days 3 and 7. Liver specimens were fixed in 10% buffered formalin solution and embedded in paraffin. Sections were made at 4 μm, stained with hematoxylin and eosin and analyzed for histological evidence of sinusoidal congestion, necrosis, and vacuolation (Monbaliu et al. (2008) *Liver Transpl.,* 14: 1256-1265). An experienced pathologist, blinded to the method of reperfusion, reviewed all biopsy samples.

Statistical Analysis

Survival curves were computed using Kaplan-Meier methods and compared using log rank tests. Mean percent changes were compared between groups across time using repeated measures ANOVA after confirming normality. Normality assumption was confirmed by constructing residual quantile-quantile (q-q) plots. Proportions were compared using the exact chi-square test. A P value of <0.05 was considered significant. Statistical analysis was performed using SAS software, version 9.1 (SAS Institute).

Results

Animal Survival

Figure 2:
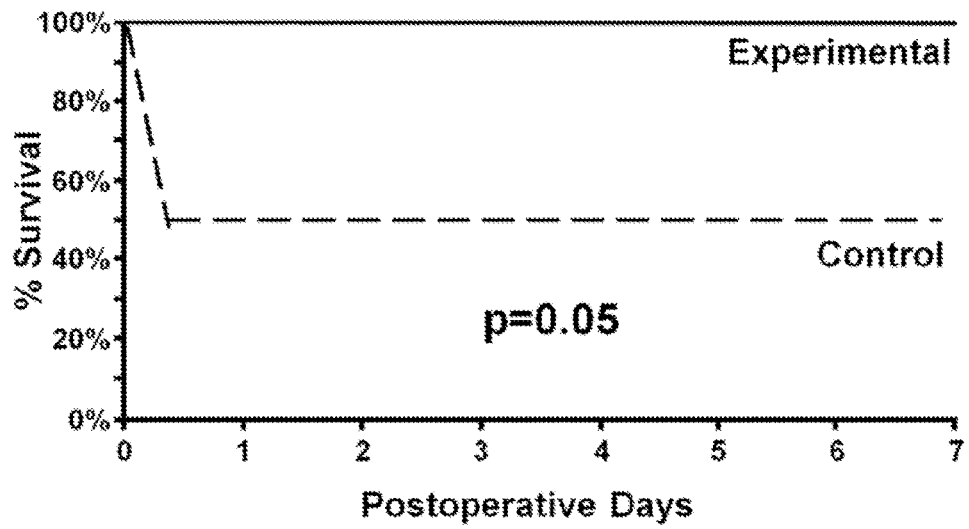
FIG. 2 shows seven-day animal survival after 2 hours of hepatic warm ischemia by type of reperfusion method.

The 7-day survival curves for the RHR and control groups are shown in FIG. 2. Survival was 100% in the RHR compared to 50% in the control. All deaths in the control group occurred within 60 minutes after liver reperfusion due to cardiac arrest refractory to resuscitation.

Hemodynamic Profile Analysis and Post-Reperfusion Syndrome

Figure 3:
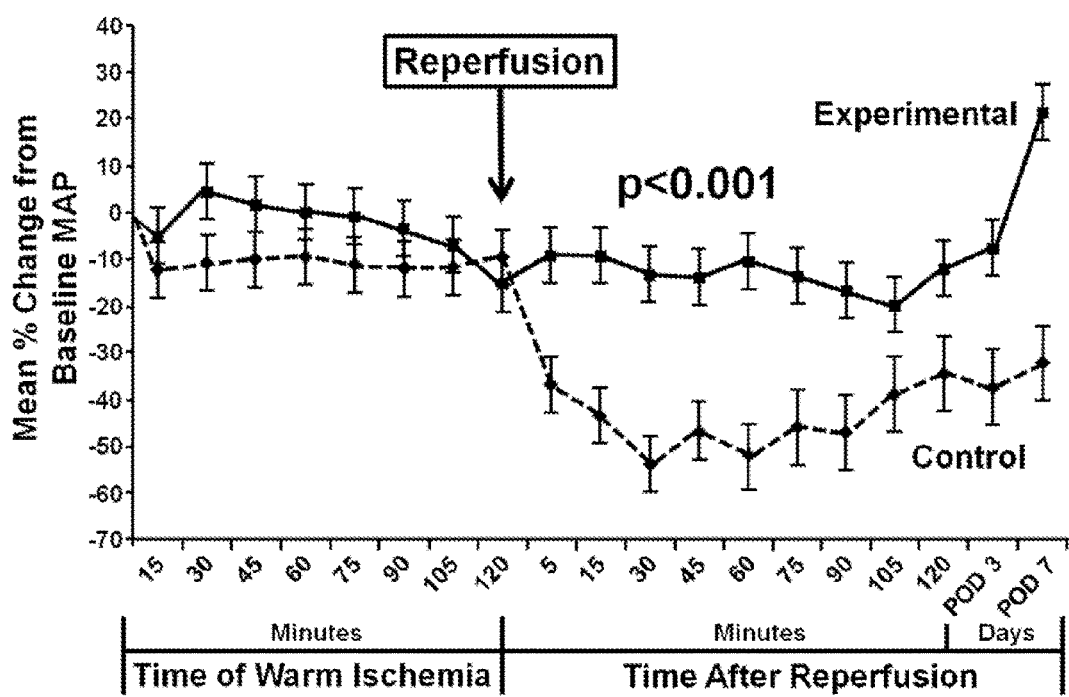
FIG. 3 shows percentage changes from baseline of mean arterial pressure (MAP) over time by type of reperfusion method.

FIG. 3 compares the effects of the two methods of reperfusion on systemic arterial pressure for the duration of the study. The percentage changes from baseline systemic arterial pressure during the 2-hour warm ischemic period were comparable between the RHR and control groups (P=0.833). However, there was a significant difference in the hemodynamic stability after reperfusion. While no animal in the RHR group developed post-reperfusion syndrome (PRS), 5 of 6 animals in the control group experienced PRS (0% vs. 83%, P=0.015). During post-operative measurements of systemic mean arterial pressure (MAP), the RHR group showed no significant change from baseline level at post-operative day 3 and improved at 7 days after reperfusion. In the control group, there was a 55% decreased in MAP from baseline at 30 minutes after reperfusion that remained below baseline level for the duration of the study (FIG. 4).

Figure 4:
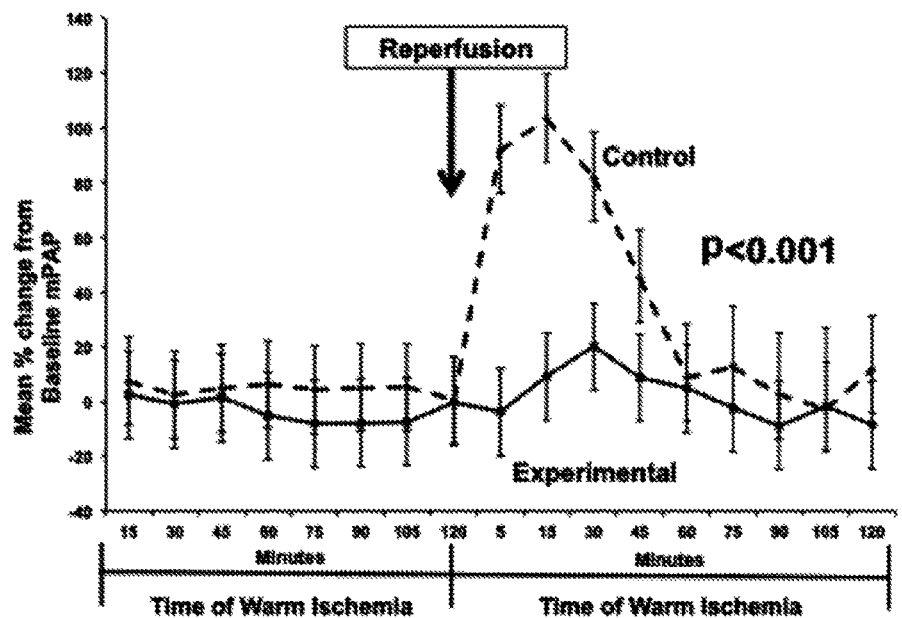
FIG. 4 shows percentage changes from baseline of mean pulmonary arterial pressure (mPAP) over time by type of reperfusion method.

As shown in FIG. 4, the percent changes of mean pulmonary arterial pressure (mPAP) from baseline were similar for both groups during the 2 hour warm ischemic period (P=0.704).

While the mPAP in the RHR group increased by 20% from baseline at 30 minutes post-reperfusion, the mPAP returned to baseline level at 75 minutes after reperfusion. In the control group, the mPAP increase by 92% at 5 minutes, by 104% at 15 minutes after reperfusion and remained elevated at 7 days after reperfusion.

Figure 5:
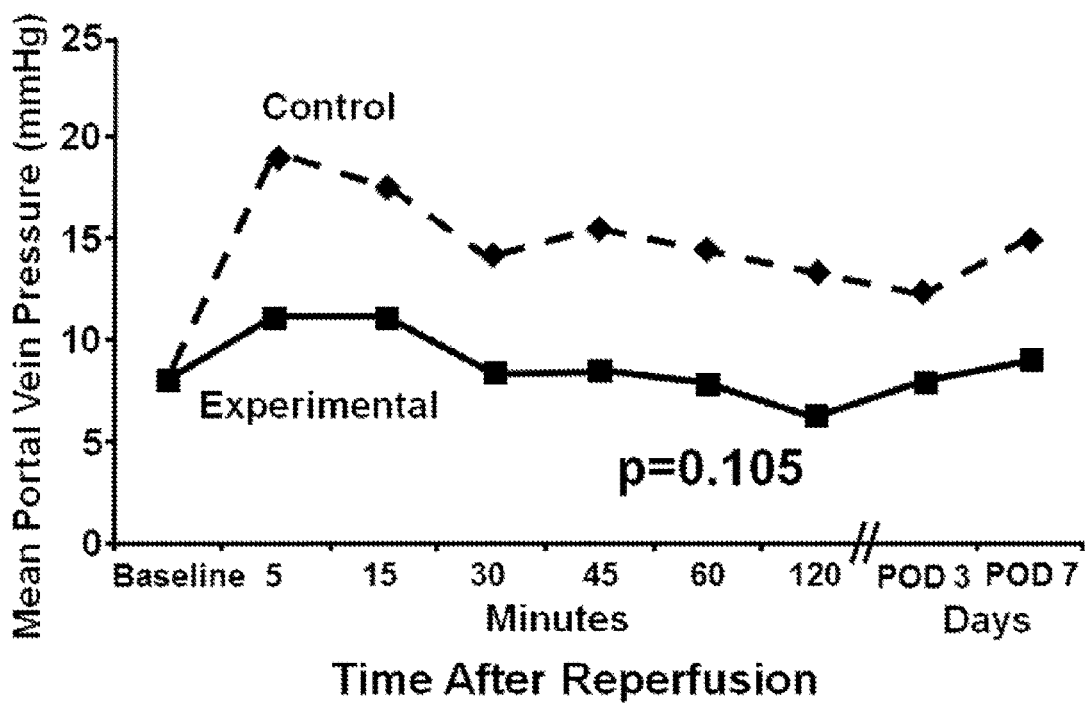
FIG. 5 shows mean portal vein pressure over time by type of reperfusion method. POD, postoperative day.

FIG. 5 compares the reperfusion and post-reperfusion portal vein pressures between the RHR and control group. In the RHR group, the mean reperfusion pressure ranged between 8-12 mmHg and was maintained after reperfusion. In contrast, the mean portal vein pressure in the control group tended to be higher during the initial and late phases of reperfusion (P=0.105).

Biochemical Analysis

Figure 6A:
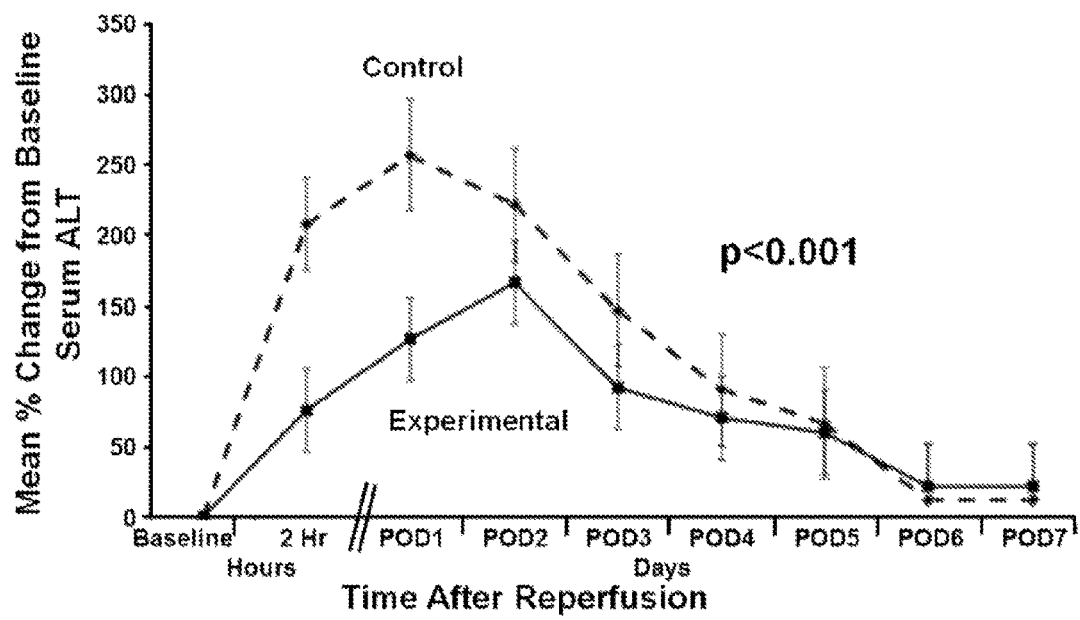
FIG. 6A shows percentage changes from baseline of serum alanine aminotransferase (ALT) over time by type of reperfusion method.
Figure 6B:
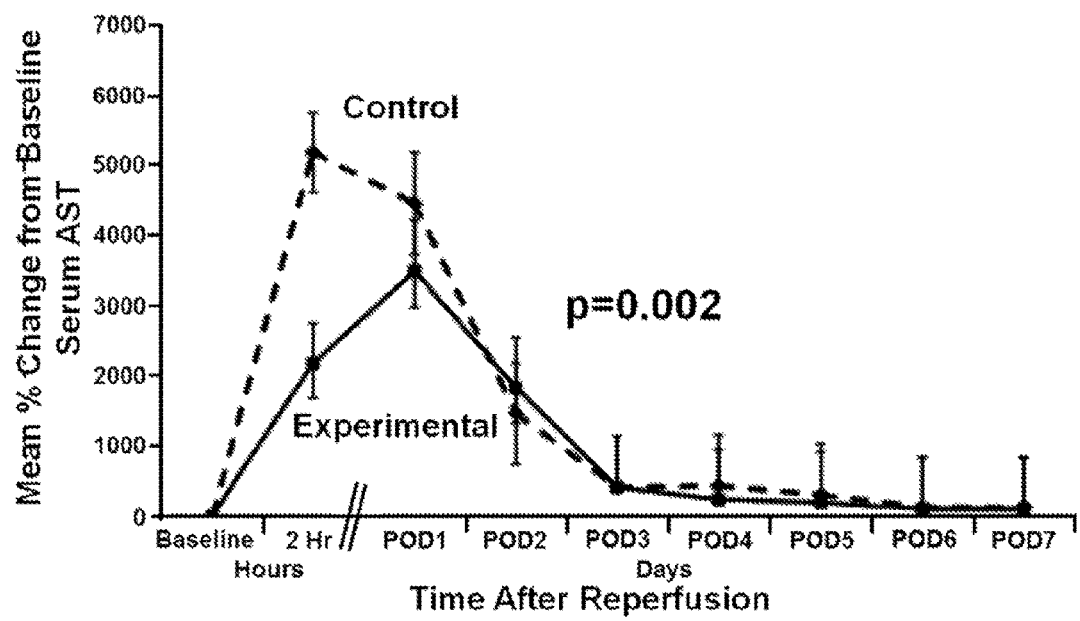
FIG. 6B shows percentage changes from baseline of serum aspartate aminotransferase (AST) over time by type of reperfusion method.
Figure 6C:
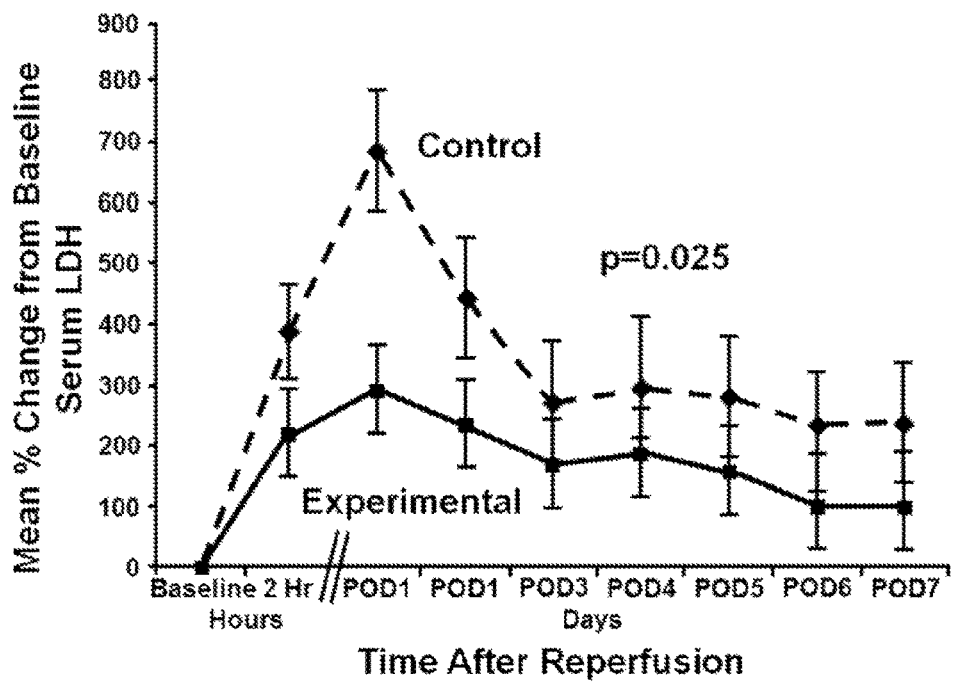
FIG. 6C shows percentage changes from baseline of serum lactate dehydrogenase (LDH) over time by type of reperfusion method. POD, postoperative day.

The degree of hepatocellular damage between the RHR and control groups are compared in FIGS. 6A-6C. The percentage changes from baseline level of serum ALT (FIG. 6A), AST (FIG. 6B), and LDH (FIG. 6C) levels were significantly lower in the RHR compared to the control group.

Neutrophil Infiltration

Figure 7:
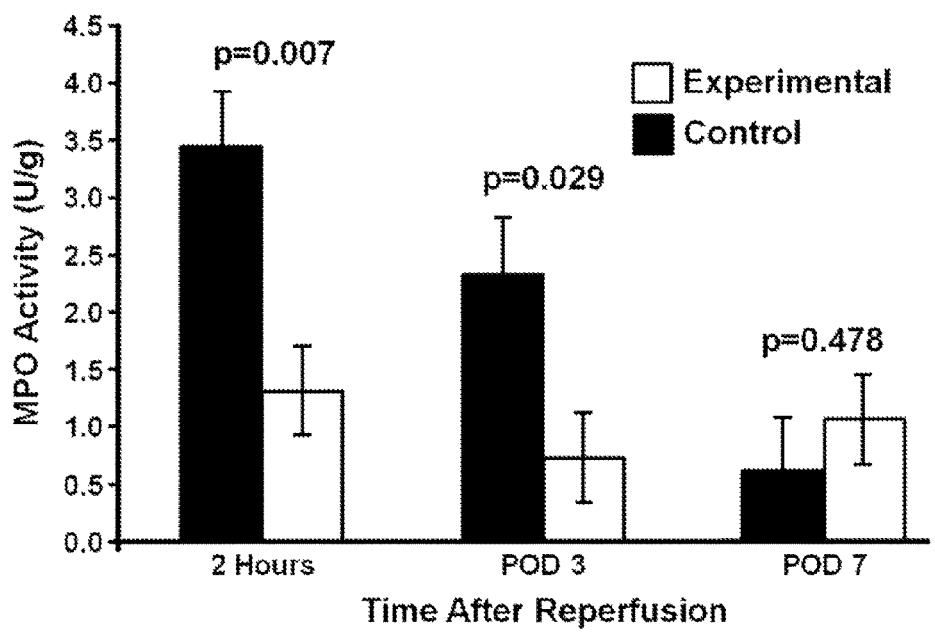
FIG. 7 shows myeloperoxidase (MPO) activities at 2 hours, 3 and 7 days after reperfusion by type of reperfusion method. MPO activity is used as an index of neutrophil infiltration in the liver tissue. POD, postoperative day.

We evaluated the role of leukocyte filtration on neutrophil infiltration within the liver parenchyma by assessing MPO activity, an index of neutrophil infiltration. MPO activity was significantly reduced in RHR treated group compared to the control group at 2 hours and 3 days after reperfusion. The MPO activity was similar on post-operative day 7 in both groups (FIG. 7).

Gross and Histological Analysis

Figure 8:
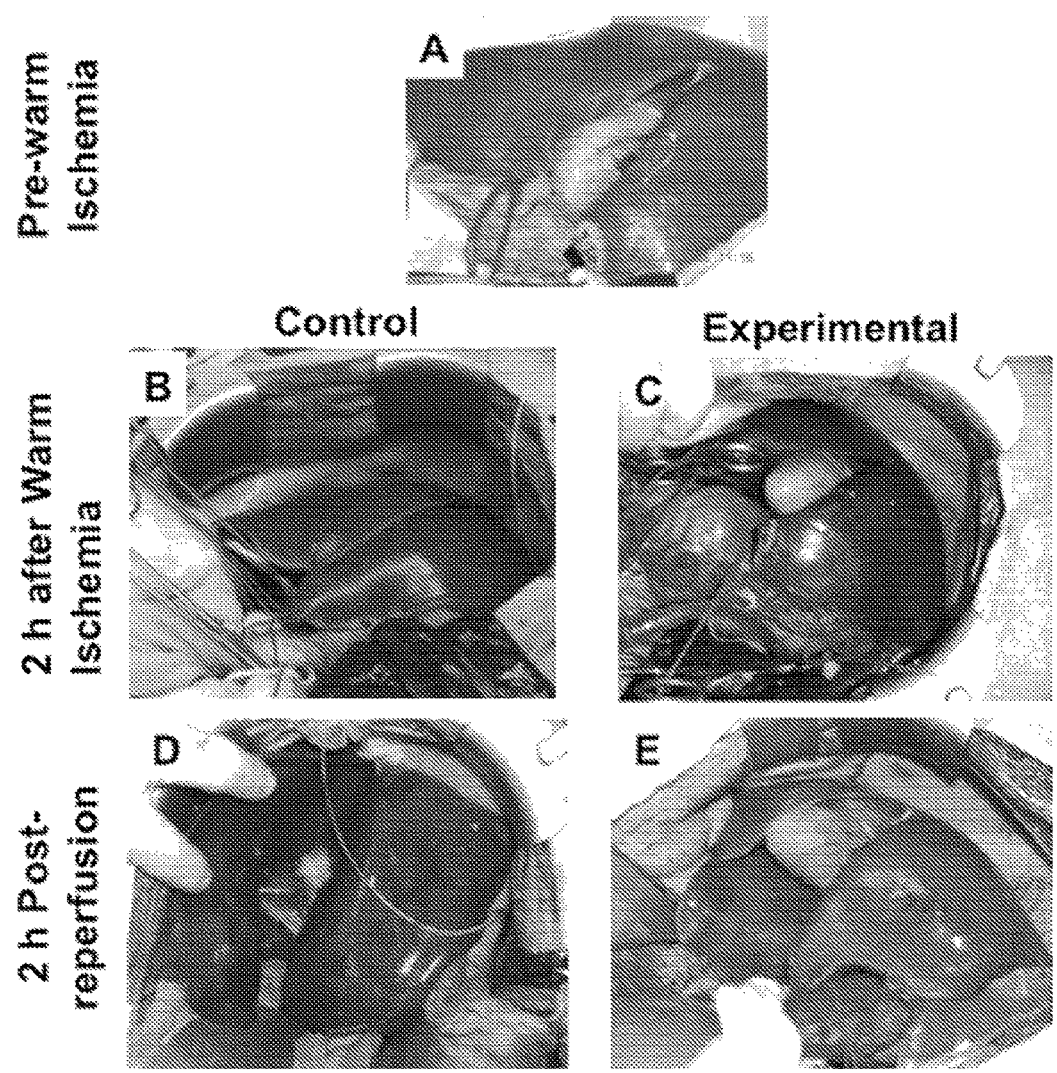
FIG. 8, panels A-E, show representative intraoperative photos of liver at different time points for both types of reperfusion methods. Panel A: Normal liver color before hepatic warm ischemia (WI). After 2 hours of WI, livers in both the (panel B) control and (panel C) experimental groups changed from normal to a dark-blue ischemic color. At 2 hours after reperfusion, the livers in the (panel D) control group remained cyanotic and the (panel E) regulated hepatic reperfusion group returned to near baseline color.
Figure 9:
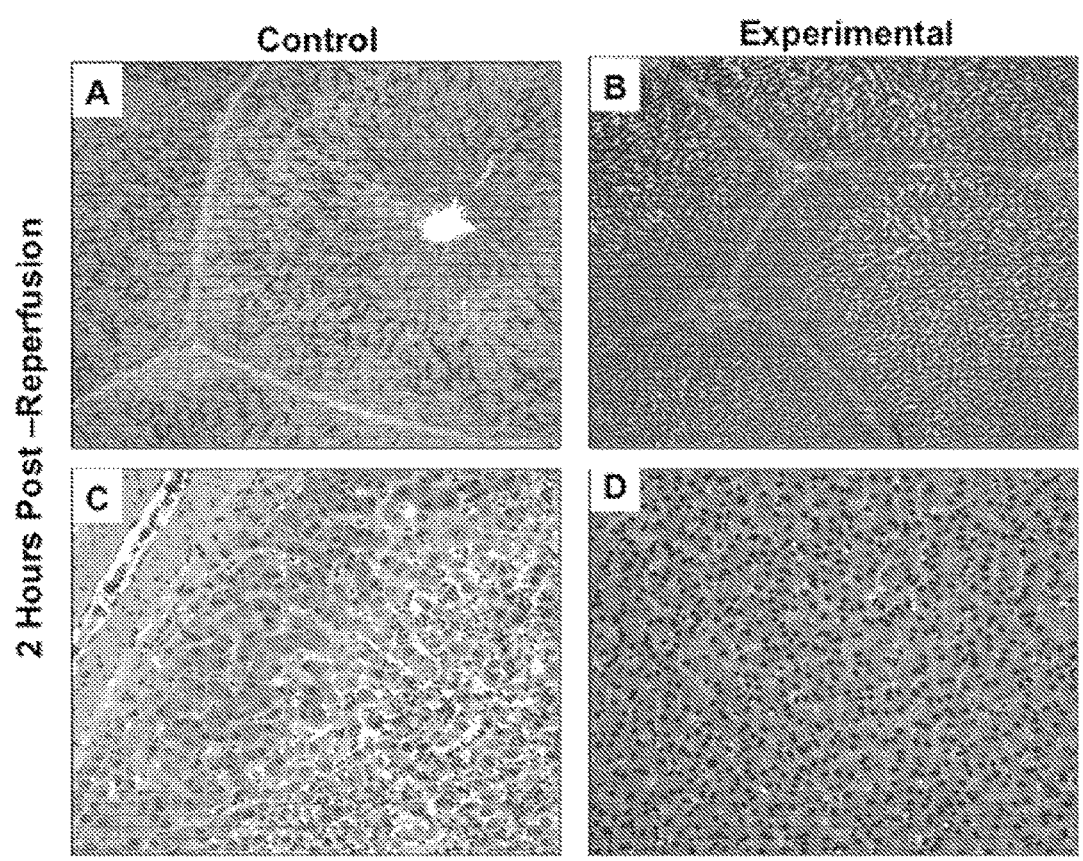
FIG. 9, panels A-D, show representative photomicrographs at 2 hours after reperfusion. At the 100× magnification, the (panel A) control group showed massive sinusoidal congestion compared with the (panel B) regulated hepatic reperfusion group. (panels C, D). At 400× magnification, (panel C) sinusoidal disruption was seen in the control group.

Representative photos of livers at different time points for both groups are shown in FIG. 8. After 2 hours of warm ischemia, livers in both groups changed from normal to a dark blue ischemic color. After reperfusion, the livers in the RHR group returned to near baseline color while the control group remained cyanotic at 2 hours post-reperfusion. Corresponding histology at 2 hours post-reperfusion are shown (FIG. 9). Compared to the RHR group, the control group showed massive sinusoidal congestion at 100× magnification. In addition, sinusoidal disruption was seen at 400× magnification in the control group.

Figure 10:
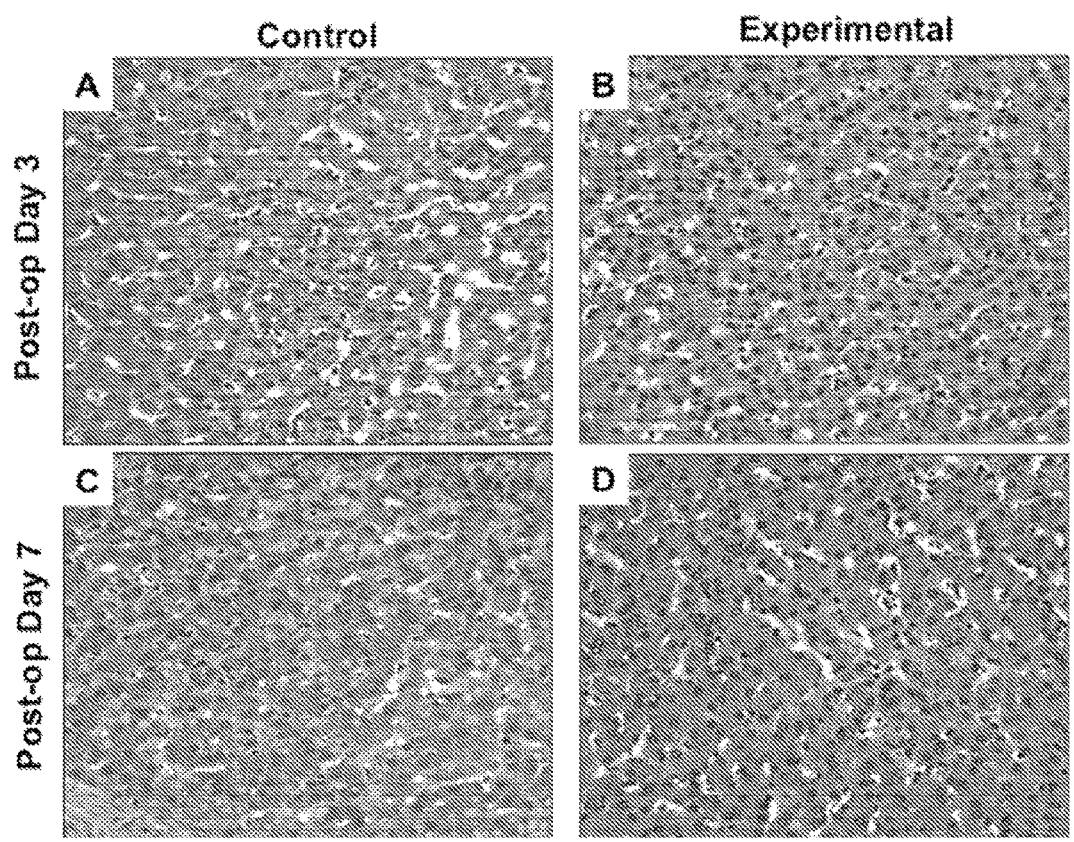
FIG. 10, panels A-D, show representative photomicrographs 3 and 7 days after reperfusion at 400× magnification. Panel A: The control group demonstrated persistent vacuolization and patchy early coagulative hepatocellular necrosis at day 3 and (panel C) patchy hepatocellular dropout and Kupffer cell hypertrophy at day 7. Regulated hepatic reperfusion-treated animal liver histology was unremarkable at postoperative days (panel B) 3 and (panel D) 7.

The histologic findings on post-operative days 3 and 7 at 400× magnification are shown in FIG. 10. At post-operative day 3, there was no demonstrable hepatocellular injury in the RHR-treated group whereas the control group showed vacuolization of 40-50% of hepatocytes and patchy coagulative hepatocellular necrosis. While the histologic findings at post-operative day 7 were normal for the RHR group, the control group demonstrated patchy hepatocellular drop-out and Kupffer cell hypertrophy.

Discussion

IRI is a dynamic process that involves interrelated and overlapping cytotoxic mechanisms resulting in ischemic organ damage and immunologically-mediated reperfusion injury. While potential interventions to mitigate the immunological and inflammatory responses to reperfusion injury of the liver have been studied (Busuttil et al. (2011) *Am. J. Transplant*, 11: 786-797; Fondevila et al. (2009) *Am. J. Transplant*, 9: 2240-2250), data on the effects of metabolic resuscitation of ischemic hepatocytes to preserve liver function remain scarce. Warm ischemia results in a state of severe cellular metabolic debt that compromises hepatocytes and makes these cells vulnerable to reperfusion injury and subsequent cell death. Previous reports in heart and lung experimental models and clinical studies showed that modification of reperfusion technique and perfusate resulted in improvement of organ function after WI (Fondevila et al. (2009) *Am. J. Transplant*, 9: 2240-2250; Beyersdorf et al. (1989) *J. Thorac. Cardiovasc. Surg.*, 98: 112-126; Schnickel et al. (2006) *J. Thorac. Cardiovasc. Surg.*, 131: 218-223; Luciani et al. (2911) *J. Heart Lung Transplant*, 30: 29-36; Halldorsson et al. (2000) *Ann. Thorac. Surg.*, 69: 198-203; discussion 4). We proposed a novel hepatocyte resuscitative concept to attenuate the adverse effects of reperfusion injury. Our study demonstrated that RHR facilitated recovery of hepatocytes from WI injury, improved liver function and survival compared to a conventional method of reperfusion in a large animal model.

The two elements of RHR are the perfusate and regulation of reperfusion milieu. The composition of the perfusate aims to replenish energy substrate, stabilize the integrity of the mitochondrial membrane, and deliver oxygen to ischemic cells. The perfusate contained tromethamine (buffers the acidotic cellular medium) (Liedtke et al. (1976) *Circulation Res.*, 39: 378-387; Castella et al. (2003) *J. Thorac. Cardiovasc. Surg.*, 126: 1442-1448), citrate, phosphate, dextrose and magnesium (reduce concentration of ionized calcium) (Fukuhiro et al. (2000) *Circulation*, 102: 319-325); aspartate and glutamate (substrates for adenosine triphosphate production during anaerobic state) (Leverve (2007) *Crit. Care Med.*, 35: S454-460); glycine (stabilizes cell membrane and inhibits inflammatory cytokines) (Sheth et al. (2011) *J. Gastroenterol. Hepatol.*, 26: 194-200); D-fructose-1,6-biphosphate (preserves the oxidative phosphorylation capacity of hepatic mitochondria and substrates for glycolysis) (Sano et al. (1995) *Gastroenterology*, 108: 1785-1792; de Fraga et al. (2011) *Transplant Proc.*, 43: 1468-1473), and whole blood. A 4:1 mixture of whole blood-to-H solution provides an oxygen carrying capacity to the perfusate. While previous studies have shown deleterious effects of high oxygen content in the generation of oxygen superoxide radicals upon reperfusion of ischemic tissues, these experiments used unmodified blood for reperfusion (McCord et al. (1985) *N. Engl. J. Med.* 312: 159-163; Parks et al. (1983) *Surgery*, 94: 428-432). Our study demonstrated that oxygen-saturated perfusate resulted in improvement of liver function after WI. A possible explanation could be that ischemic cells receiving a substrate-enriched perfusate require higher quantity of oxygen to maintain metabolic function compared to cells that receives unmodified host blood.

Migration of leukocytes during the initial stages of reperfusion is a key event in acute inflammatory liver injury and contributes to tissue dysfunction during reperfusion (Jaeschke and Hasegawa (2006) *Liver Int.*, 26: 912-919; Gopalan et al. (1997) *J. Immunol.*, 158: 367-375; Rothlein et al. (1986) *J. Immunol.*, 137: 1270-1274). Leukodepletion has been reported to reduce leukocyte-medicated injury in experimental models (Fruhauf et al. (2004) *Eur. Surg. Res.*, 36: 83-87; Wamser et al. (2993) *Transplant Int.*, 16: 191-196) and clinical lung transplantation (Schnickel et al. (2006) *J. Thorac. Cardiovasc. Surg.*, 131: 218-223; Lick et al. (2000) *Ann. Thorac. Surg.*, 69: 910-912). Our findings also support the beneficial role of leukocyte filtration in reducing neutrophil infiltration in the liver parenchyma during the early cellular recovery. Compared to the control group, there was a significant reduction of MPO activity in the RHR group from the time of liver reperfusion to 3 days after revascularization.

RHR also addresses the important role of cellular environment (reperfusion pressure, temperature pH) on hepatocyte viability upon revascularization. The optimal hepatic reperfusion pressure to facilitate hepatocyte recovery and minimize further sinusoidal endothelial injury has been unclear. While high reperfusion pressure aggravates the ischemic injury to sinusoidal endothelial cells, it is imperative to have a perfusion pressure that could overcome the flow resistance present in an ischemic organ for complete delivery and distribution of perfusate to all areas of the liver. We regulated the hepatic reperfusion pressure between 8-12 mmHg during the initial reperfusion phase to avoid exposure of ischemic hepatocytes to high portal reperfusion pressure due to stagnation of splanchnic circulation commonly seen in cirrhotic patients and during the anhepatic phase of liver transplantation. Reperfusion pressure of the liver within this range resulted in compete distribution of perfusate in the liver (FIG. 8) and excellent liver function.

The effects of varying temperatures on cellular metabolic activities have been studied extensively (Biberthaler et al. (2001) *Transplantation*, 72: 1486-1490). To attenuate ischemic injury, hypothermia is used for the preservation of liver grafts and has been applied during hepatic resection under total hepatic vascular exclusion (Fortner et al. (1974) *Ann. Surg.*, 180: 644-652; Hannoun et al. (1996) *J. Am. Coll. Surg.*, 183: 597-605). Previous studies reported that moderate hypothermia (26° C. to 34° C.) effectively protects the liver microcirculation during liver WI compared to hypothermia at 4° C. (Biberthaler et al. (2001) *Transplantation*, 72: 1486-1490; Heijnen et al. (2003) *Surgery*, 134: 806-817). Our technique allowed regional delivery of moderate hypothermia to the liver while maintaining the core body temperature of the animal within physiologic range, an aspect of RHR that can readily be applied in the clinical setting.

The present study aims to address an important practice gap in the mitigation hepatic IRI from a prolonged period of WI injury. The experimental design utilized a swine model because it shares similar hepatic and cardiovascular physiology with humans and thus, information gained would facilitate transfer of its application to various clinical settings. During hepatic surgery, RHR may allow a longer period of portal inflow occlusion (Pringle maneuver) to minimize intraoperative blood loss and improve post-operative liver function. When organs from marginal or extended criteria donors are used in LT, RHR could be used to resuscitate these grafts prior to reperfusion of the patient's portal venous blood. This method could also be applied during deceased donor organ procurement after cardiac death, instituting RHR after asystole to reverse donor WI injury prior organ preservation and storage. In addition to its potential benefits in attenuating hepatic IRI, RHR could also provide a platform for delivery of new molecules or agents that have synergistic or additive properties in mitigating IRI. Lastly, further investigation on the use of an artificial oxygen-carrying blood substitute in place of the blood component of the perfusate would have clinical application.

In conclusion, the conventional method of liver reperfusion after a period of WI exposes ischemic cells to endotoxin-rich host portal blood under elevated portal pressure resulting in a severe hepatic IRI and cellular necrosis. We propose a novel organ resuscitative strategy after WI using an energy substrate-enriched, leukocyte-depleted, oxygen-saturated perfusate delivered in a pressure, and temperature-controlled milieu to attenuate IRI. Our study shows that RHR mitigates IRI, facilitates liver function recovery and improves survival after prolonged warm ischemia. This novel strategy has applicability to clinical hepatic surgery and liver transplantation, particularly when marginal grafts are used.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A hepatic reperfusion protection solution, said solution consisting of:
   a tromethamine buffer;
   one or more substrates for the synthesis of adenosine triphosphate (ATP) under anaerobic conditions;
   citrate-phosphate-dextrose (CPD);
   one or more amino acids that stabilize cell membranes;
   D-fructose-1,6-biphosphate; and
   magnesium sulfate;
   wherein the pH of said organ reperfusion protection solution ranges from about pH 7.5 to about pH 8.8; and
   wherein said solution is effective to improve liver function recovery after warm ischemia.

2. The hepatic reperfusion solution of claim 1, wherein the pH of said solution ranges from about pH 8.1 to about pH 8.4.

3. The hepatic reperfusion protection solution of claim 1, wherein said one or more substrates for the synthesis of ATP is aspartate and/or glutamate.

4. The hepatic reperfusion protection solution of claim 1, wherein said one or more amino acids that stabilize cell membranes is one or more amino acids selected from the group consisting of glycine, lysine, and aspartic acid.

5. The hepatic reperfusion protection solution of claim 1, wherein:
   said one or more substrates for the synthesis of adenosine triphosphate is 1-monosodium glutamate and 1-monosodium aspartate; and
   said one or more amino acids that stabilize cell membranes is glycine.

6. The hepatic reperfusion protection solution of claim 5, wherein:
   said citrate-phosphate-dextrose is a combination of citric acid monohydrate, sodium citrate dehydrate, dextrose, and sodium phosphate monobasic monohydrate; and
   said D-fructose-1,6-biphosphate is D-fructose-1,6-bisphosphate trisodium salt, octahydrate.

7. The hepatic reperfusion protection solution of claim 6, wherein:
   said magnesium sulfate ranges from about 10 g to about 14 g per liter of solution;
   said tromethamine ranges from about 7 g to about 9 g per liter of solution;
   said citric acid ranges from about 0.5 g to about 1.0 g per liter of solution;
   said sodium citrate ranges from about 5 g to about 7 g per liter of solution;
   said sodium phosphate ranges from about 0.25 g to about 0.75 g per liter of solution;
   said D-fructose-1,6-bisphosphate ranges from about 4 g to about 8 g per liter of solution;
   said L-monosodium glutamate ranges from about 8 g to about 12 g per liter of solution;
   said L-monosodium aspartate ranges from about 8 g to about 12 g per liter of solution; and
   said glycine ranges from about 0.2 g to about 0.6 g per liter of solution.

8. The hepatic reperfusion protection solution of claim 1, wherein per liter of solution, said solution consists of:
   about 12.01 g magnesium sulfate;
   about 8.1 g tromethamine;
   about 0.73 g citric acid;
   about 5.91 g sodium citrate;
   about 0.49 g sodium phosphate;
   about 5.50 g D-fructose-1,6-bisphosphate;
   about 5.22 g dextrose;
   about 10.7 g 1-monosodium glutamate;
   about 9.8 g 1-monosodium aspartate;
   about 0.36 g glycine; and
   sterile water, q.s. 1,000 mL.

9. The hepatic reperfusion protection solution of claim 1, wherein said solution is sterile.

10. A composition consisting of the hepatic reperfusion protection solution of claim 1 mixed with whole blood.

11. The composition of claim 10, wherein the ratio of blood to hepatic reperfusion solution ranges from about 1:1 to about 10:1.

12. The composition of claim 10, wherein leukocytes in the composition are reduced.

13. A composition consisting of the hepatic reperfusion protection solution of claim 1, wherein said solution is oxygenated.

* * * * *